(12) United States Patent
Aeby et al.

(10) Patent No.: US 8,540,511 B2
(45) Date of Patent: Sep. 24, 2013

(54) METHOD AND DEVICE FOR DETERMINING THE APICAL POSITION IN A DENTAL ROOT CANAL

(75) Inventors: Francois Aeby, Montagny (CH); Pierre-Andre Farine, Neuchatel (CH); Roman Merz, Neuchatel (CH); Cyril Botteron, Gals (CH)

(73) Assignee: Maillefer Instruments Holding SARL, Ballaigues (CH)

( * ) Notice: Subject to any disclaimer, the term of this patent is extended or adjusted under 35 U.S.C. 154(b) by 337 days.

(21) Appl. No.: 12/934,181

(22) PCT Filed: Apr. 7, 2008

(86) PCT No.: PCT/IB2008/000820
§ 371 (c)(1),
(2), (4) Date: Sep. 23, 2010

(87) PCT Pub. No.: WO2009/125237
PCT Pub. Date: Oct. 15, 2009

(65) Prior Publication Data
US 2011/0039227 A1  Feb. 17, 2011

(51) Int. Cl.
*A61C 19/04* (2006.01)
(52) U.S. Cl.
USPC .......................................................... 433/72
(58) Field of Classification Search
USPC ................ 433/72, 75, 224; 33/513; 600/547
See application file for complete search history.

(56) References Cited

U.S. PATENT DOCUMENTS

| 5,080,586 A | | 1/1992 | Kawai |
| 5,096,419 A | * | 3/1992 | Kobayashi et al. ............. 433/72 |
| 6,059,569 A | | 5/2000 | Otsuka |

FOREIGN PATENT DOCUMENTS

| JP | 62025381 B | 7/1985 |
| JP | 62002817 B | 9/1985 |
| WO | 0147414 A1 | 7/2001 |

OTHER PUBLICATIONS

International Search Report, dated Dec. 16, 2008, from corresponding PCT application.

* cited by examiner

*Primary Examiner* — Sunil K Singh
(74) *Attorney, Agent, or Firm* — Young & Thompson

(57) ABSTRACT

An apex-locating method and device for determining the depth position of the apex in a dental root canal. It uses a device making it possible to form a circuit including a first probe electrode inserted into the root canal of a tooth, a second electrode in conductive contact with an oral mucous membrane, frequency-generating elements able to produce alternating electrical signals at a number of frequencies, and elements for measuring electrical magnitude of alternating signals in the circuit. Provision is made for exciting the circuit and measuring the levels of magnitude of the alternating signals, respectively at low frequency and at high frequency and for detecting a point of intersection where the two levels measured at low and high frequencies meet and become substantially equal, these frequencies being sufficiently far apart for this point of intersection to exist. This point gives the position of the apex.

19 Claims, 21 Drawing Sheets

METHOD AND DEVICE FOR DETERMINING THE APICAL POSITION IN A DENTAL ROOT CANAL

The present invention relates to the area of apex-locating methods and devices which are used in endodontics to locate, in a root canal of a tooth, the position of the apex in terms of depth, i.e. the position of the summit of this root (i.e. apical terminus) and, more precisely, the end of the orifice of the apical foramen at the bottom of the root canal.

During dental surgery procedures, in particular during a procedure to clean and shape the root canal, the apex locators serve to avoid crossing the apical foramen, i.e. passing the apical terminus and to keep the subjacent maxillary ligament with its nerve bundles from being reached.

FIG. 1 shows the anatomical structure of a tooth in a schematic view along a plane of cut along the axis of the canal of a root of the tooth. Certain teeth, such as the molars and premolars, can have a number of roots RT or at least several root canals CR which may be separate or joined.

The end of the root RT is pierced by an orifice FA known as the apical foramen for passage of nerve bundles and vessels. Sometimes, as shown in FIG. 1, this orifice FA at the end of the root canal CR narrows to form a bottleneck at the apical constriction CA (narrow neck permitting passage of the group of vessels and nerves which irrigate the pulp). In other cases (not shown) the root canal has a large cross-section with no narrowing.

At this apical constriction CA, there is located the cement-dentine joining interface CT/IV, an interface between mineral substances (cement/dentine) which have contrasting electrical properties.

During endodontic surgical procedures, such as procedures for cleaning and shaping the dental canal CR, dentists seek to remove all materials, debris and organic fluids which fill the root canal CR right to the bottom, i.e. as far as the end of the apical foramen FA, in order to avoid a dental abscess recurring in the root canal CR.

However, the dentist's objective is principally, as far as possible, not to pass the apical terminus APX, on the one hand, so as not to cause the patient any pain and, on the other hand, so as not to hollow out a cavity below the root, beyond the apex, which could give rise to the development of an abscess.

It is thus of the greatest importance for the dentist to locate the foramen FA and apical terminus APX very precisely.

As indicated in FIG. 1, radiographic images of the teeth taken along the horizontal plane XRA of the jaw generally give an incorrect radiographic position for the apex which does not correspond to the true position of the directing plane of the anatomical apex AA.

Electronic apex-locating devices have been developed for the past fifty years to locate the end of the root canal in a precise manner, being based on the changes in electrical properties in this transition zone.

The first generations of apex locators, developed by Sunada on the basis of the work of Pr. Suzuki, operate on a principle of resistance measurement in the root canal, being based on the observation that when the apical zone is crossed, the resistance value drops suddenly and crosses a resistance threshold of about $R=6.5$ k$\Omega$, a value which is substantially constant from one individual to another.

As shown in FIG. 2A, the resistance is measured between a first electrode ES formed by an endodontic file or probe inserted into the root canal CR and a second electrode EM shaped to be brought into close electrically conductive contact with an oral mucous membrane (lip, gum . . . ).

FIG. 2B indicates that the resistance R first drops slightly as the endodontic file ES is pressed in to a depth DP within the root canal CR on the axis of the tooth, then R drops sharply when the apical zone is crossed, before returning to a base value once the apical terminus has been passed.

Sunada established that the apex is located in the zone where the resistance crosses the threshold value $R=6.5$ k$\Omega$, a value which is substantially constant from one individual to another.

U.S. Pat. No. 5,096,419 in the name of Kobayashi of the company MORITA cites two prior art Japanese documents JP 2817/62 and JP 25381/62 relating to two series of measuring devices making it possible to locate the position of the apex and to determine the depth of the root canal.

The first series of devices is based on a resistance measuring principle using direct current, the continuous resistance dropping sharply when the apical zone is crossed.

The second series of devices is based on an impedance measuring principle, resistance generalisation, but with measurement using an alternating signal and including two resistive and capacitive components; the alternating signal impedance drops when the point of the probe approaches the apex.

The first resistance measuring principle only makes it possible to detect when the apical terminus is passed, which does not satisfy the dentist's objective of being warned before having passed the apex.

The second impedance measuring principle should prove to give more warning because the impedance is supposed to drop when there is a change in properties at the cement/dentine interface CT/IV when the apical constriction CA is being crossed, this being at a location before the directing line AA of the apex is reached as shown in FIG. 1.

A first disadvantage is that this second measuring principle, based on the detection of a drop in impedance at the cement/dentine junction of the apical constriction does not work on children and young patients because their teeth have little or no hypermineralised dentine.

In general, these two series of devices necessitate delicate rating and calibration operations, operations which are imprecise, tedious and a source of error.

In practice, and speaking generally, these two series of apex locators have the disadvantage of indicating the position of the apex only after the point of the electrode probe has crossed the apical constriction. The resistance measurements do not drop before the point of the probe has passed the apical terminus APX. In fact it proves to be the case that the impedance measurements drop only when the point of the file has passed the orifice of the apical foramen FA and touches the ligament below the dental root RT. However, dentists seek most particularly not to cross the apical foramen FA.

Another considerable problem is that the two measuring principles of these two series of apex locators have the disadvantage that the resistance/conductance measurements become wholly imprecise, even nonsensical, in the presence of conductive fluids in the root canal.

During dental cleaning and shaping procedures the canal is generally filled with fluids and materials, in particular organic bodies and matter (saliva, blood, lymph, serum, physiological fluids, organic debris) which behave like slightly salty media which are thus fairly conductive, analogous to what is known as physiological liquid or serum (common aqueous saline solution of 0.9% NaCl) which is a moderately conductive ionic solution like seawater.

Furthermore, dentists have to continually clean the mouth of the patient with a flow of rinsing liquid based on a conductive saline solution of NaCl, and especially with disinfectant solutions, in particular Dakin's liquid ("neutral diluted solute of sodium hypochlorite", NaClO diluted to 2.5% or 5%, similar to true Javel water) which is a very highly conductive ionic solution (OH-ions). Such highly conductive ionic solutions totally disrupt conductivity measurements (resistance, impedance) and entirely invalidate any determination of the position of the apex.

The on-going presence of such organic fluids and solutions during dental procedures precludes the use of apex-locating devices based on such resistance or conductance measuring principles.

The improvement of this prior art proposed by Kobayashi in document U.S. Pat. No. 5,096,419 involves comparing two conductance measurements effected at two distinct frequencies f and 5f as shown in FIG. 3 in order to be unencumbered by fluctuations in conductivity caused by the presence of ionic solutions.

According to this third measuring principle, measurements of voltage (V) are carried out at the terminals of a reference resistor R=5 kΩ placed in series with the electrodes. The series circuit is supplied by a generator of square signals at the frequency f, which produces harmonic signal components at the frequencies fa=f and fb=5f. In a first time period (phase I) during the insertion of the probe into the root canal, the voltage measurements A and B taken at the two frequencies fa=f and fb=5f remain stable. In a second time period (phase II), the two voltage measurements A' and B' increase as a zone II corresponding to the apical constriction is being crossed (because the impedance of the canal drops as the cement/dentine junction is approached).

According to document U.S. Pat. No. 5,096,419 of Kobayashi, the two curves A' and B' are not equidistant in zone II but their deviation Γ decreases.

According to Kobayashi the difference δ between the two voltage measurements A and B (δ=A−B), initially of the substantially constant value −Γ in zone I, would decrease in zone II.

Kobayashi states that in zone II, the deviation B−A or the difference δ=A−B comes closer to an extremum value (minimum deviation) before shifting suddenly in the other direction and becoming more separate again. The extremum, i.e. the point ΔX where the deviation |B −A| is minimum (i.e. δ=A−B max.) corresponds to the position of the apex according to the teaching of U.S. Pat. No. 5,096,419.

Document U.S. Pat. No. 5,096,419 then describes a sophisticated electronic circuit for threshold detection in order to determine at which point the difference δ=A−B between the two voltages measured at the two frequencies fa=f=1 kHz and fb=5f=5 kHz crosses a threshold value θ corresponding to the position of the apex.

The disadvantage of this device is that the fixing of the threshold value θ still necessitates calibration operations which are delicate, imprecise and a source of error. In practice, the precise course of the variations in the curves A and B and their deviation |δ|=|A−B| are eminently variable according to the individual concerned and the electrical conditions prevailing in each root canal.

For each individual canal of each root of each tooth it is necessary to recommence the rating and calibration operations, operations which are specialised, time-consuming and tedious for the dentist and which make these devices unattractive for the dentist to use.

In fact, depending on whether the threshold is fixed at a value θ below the extremum or at a value θ' beyond the extremum, either the measurement of the position P of the apex AX is imprecise and encumbered with an error c, or no crossing of the threshold is detected and the device does not signal that the probe is passing the apical terminus.

Generally speaking, this third principle of detecting a difference in measurements made at two frequencies also has the disadvantage of not setting an absolute measuring criterion for the position of the apex.

The detection of the crossing of a threshold still has the disadvantage of being relative to the setting of an arbitrary threshold value.

From another point of view, if it were desired to detect the point ΔX of turning back, i.e. the point of inflexion AX where the curve δ=A−B reaches the extremum and changes the direction of variation, which would constitute an absolute criterion, it would nevertheless be necessary to pass the point AX, i.e. to cross the apical terminus in order to detect the passage at the extremum and the change in the direction of variation.

FIG. 4 illustrates a fourth apex-locating principle proposed by document U.S. Pat. No. 5,080,586 in the name of Kawai of the OSADA Institute.

Document U.S. Pat. No. 5,080,586 describes a measuring system comparable to that of document U.S. Pat. No. 5,096,419 and consisting of applying two alternating voltages $V_1$ and $V_2$ having two distinct frequencies $f_1$ and $f_2$ to the terminals of a circuit comprising two electrodes (a needle inserted into the root canal of a tooth and an electrode in contact with an oral mucous membrane) in series with a measuring resistor.

It is the case that the two frequencies $f_1$=1 kHz and $f_2$=5 kHz proposed by document U.S. Pat. No. 5,080,586 are identical to the two frequencies fa=f=1 kHz and fb=5f=5 kHz used according to the teaching of the other document U.S. Pat. No. 5,096,419.

On the other hand, according to FIG. 4 which shows the course of the measurement curves of document U.S. Pat. No. 5,080,586 of the prior art, the measurement curves of the two voltages $V_1$ and $V_2$ taken at the two frequencies $f_1$=1 kHz and $f_2$=5 kHz diverge and move apart continuously with the depth P of insertion of the electrode, the deviation ($V_2$−$V_1$) increasing monotonously.

The points of view on the course of the voltage curves plotted at the two frequencies of f=1 kHz and 5f=5 kHz are thus divergent and show the degree to which the measurements are errant, unreliable and do not constitute an absolute measurement criterion for precisely determining the position of the apex.

In order to determine the position of the apex, the document U.S. Pat. No. 5,080,586 proposes determining the ratio between these two voltages V1 and V2 plotted at the two frequencies $f_1$ and $f_2$ (ratio V2/V1) and determining a threshold value, the position of the apex A corresponding to the crossing of this threshold by the ratio V2/V1.

This alternative measuring principle still has the disadvantage of not constituting an absolute criterion for determining the exact position of the apex but of referring to relative threshold values, varying according to the individuals concerned and the electrolytic conditions prevailing in each root canal, which means that the dentist has to perform calibration operations which are delicate, imprecise and a source of error.

More generally, these latter apex-locator generations are based on principles of measuring voltage at the terminals of a reference resistor in series with the two electrodes which reflect the conductance (inverse of the impedance) existing in the root canal between the electrodes.

The problem is that such measuring principles are directly affected by the presence of conductive fluids in the root canal which entirely invalidate the determination of the position of the apex.

As already mentioned, the presence of conductive fluids in the root canal is inevitable in dental surgery procedures because of the presence of fluids and organic materials (blood, lymph, saliva, serum, organic debris) and the necessity of cleaning the mouth with rinsing solutions (physiological liquid, i.e. 0.9% NaCl solution) or with disinfectant solutions (Dakin's liquid, i.e. NaClO solution).

Moreover, another general problem of the apex-locating devices based on measurements of impedance in the root canal of the tooth is that they do not permit resolution of complex teeth having several root canals or root canals with bifurcations or aberrations (multiple, forked, branched or twin roots, excrescences . . . ).

The molars have several roots and root canals which are generally well separated. The premolars and molars generally have twin roots, just subdivided at their end by a bifurcation into two twin (forked) root canals. Other teeth may have branches or aberrations. The teeth which generally are most subjected to dental surgery and endodontic cleaning and shaping procedures are precisely these complex teeth, notably the molars and premolars.

The object of the invention is thus to provide a means of apex location which solves these problems and overcomes the disadvantages of prior art apex locators.

The object of the invention is to develop means for detecting the position of the apex based on a criterion of absolute measurement of the depth of the apex, no longer requiring the arbitrary setting of relative thresholds which are dependent on the patient or on fluctuations in the characteristics of the root canal.

The object of the present invention is thus to produce a system, device or method for apex location making it possible to determine the position of the apex with a good level of precision regardless of the configuration or the conditions presented by the root canals of the teeth.

The object is in particular to be able to determine precisely the position of the apex while being as little sensitive as possible to the presence of conductive fluids and especially rinsing solutions, organic bodies or physiological liquids analogous to the presence of common saline solution based on sodium chloride (0.9% NaCl), as well as ionic disinfectant solutions such as Dakin's liquid based on sodium hypochlorite (2.5% or 5% NaClO) used systematically during dental surgery procedures, in particular for endodontic abscess curage procedures.

Another object is to create a method and device for apex location permitting resolution of teeth with complex root canals, i.e. making it possible to recognise, single-out and determine the position of the end of each root canal of the tooth with a good level of precision with the greatest possible improvement over the previously commercially available devices.

One particular object is to produce an apex-locating system providing a determination of the position of the apex with not only a low level of error with respect to the actual position of the apical terminus but also permitting the position of the apex to be indicated before the apical terminus is reached or passed.

Stated briefly, the invention provides using an endodontic device conventionally comprising two electrodes, one in connection with a file or a metal probe able to be inserted in the root canal of a tooth, the other able to be brought into closely conductive, low-impedance, electrical contact with an oral mucous membrane, the two electrodes being incorporated in series in a circuit supplied by a frequency-agile alternating signal generator and comprising an assembly for measuring the amplitude of the alternating signals. The assembly comprises, in particular, a voltage amplitude measuring device for the alternating signals at the terminals of a measuring reference resistor in series with the electrodes and the frequency-agile generator supplying this series circuit, which amounts to measuring the amplitude of the alternating current passing through the reference resistor and the electrodes. According to the invention the amplitude of the alternating signals is plotted at widely diverse frequencies belonging to opposing frequency bands as permitted by the extent of the frequency ranges of the frequency-agile generator.

According to the invention the amplitude levels of the signals plotted at two defined frequencies intersect when passing the apical constriction, i.e. depending on the insertion of the probe electrode at depth into a root canal of a tooth and during the course of this insertion, a number of phases, zones and/or hierarchies are distinguished as follows:

initially, during introduction of the probe, at the start of the crown-like part of the tooth ("crown"), the first signal amplitude level plotted at a lower frequency (low frequency f) is clearly higher than the other amplitude level plotted at the higher frequency (high frequency F), then as the probe is being introduced into the root canal of the tooth, the two amplitude levels of the signals plotted at the two defined frequencies (opposing low and high frequencies f & F) increase as the end of the root canal is approached, in a transition zone, which corresponds to passage of the apical constriction, at the end of the root canal, the second amplitude level plotted at the higher frequency (high frequency F) comes closer to, meets and becomes substantially equal to the first amplitude level plotted at the lower frequency (low frequency f), up to the point of exactly coinciding with it, and possibly (if one continues), after the apical constriction zone is passed, the second signal amplitude level plotted at the higher frequency (high frequency F) becomes greater than, or even clearly exceeds, the first amplitude level plotted at the lower frequency (low frequency f).

Of course, for the dentist it is out of the question to seek to pass the apical terminus and thus reach the zone where the second amplitude level plotted at the higher frequency (high frequency F) would become greater than the first amplitude level measured at the lower frequency (low frequency f).

Thus in an advantageous manner the invention provides a criterion for absolute measurement of the position of the apical constriction which corresponds to the point where the two amplitude levels determined at the two defined frequencies (low and high frequencies f and F) intersect or at least meet and become substantially equal and/or coincide.

In order to achieve the objects mentioned above there is provided, according to the invention, an apex-locating method to determine a measurement of the depth position of the apex in a root canal of a tooth, using a device having a first conductive electrode forming an endodontic probe able to be inserted into the root canal of a tooth, a second electrode shaped to be brought into electrically conductive contact with an oral mucous membrane, frequency-generating means able to produce alternating electrical signals at a number of frequencies, and means for measuring the magnitude of alternating electrical signals in a circuit comprising the said frequency generator, the first probe electrode inserted into the root canal and the second electrode in contact with the oral mucous membrane, the method comprising the steps of:

exciting the circuit and measuring the magnitude levels of the alternating electrical signals in the circuit, at a lower frequency and a higher frequency respectively;

detecting a point of coincidence where two respective levels of the electrical magnitude measured at the said lower and higher frequencies meet and are substantially equal, the said lower and higher frequencies being sufficiently far apart for such a point of coincidence to exist, the said point of coincidence corresponding to the position of the apex.

Provision is preferably made for measuring amplitude levels of the electrical signals applied to the circuit and more precisely the intensity of the current passing through the electrodes, in particular by measuring absolute voltage amplitude values of the electrical signals at the terminals of a resistor in series with the electrodes.

The invention is also implemented with an apex-locating device for determining the depth position of the apical constriction in a dental root canal, the device comprising a terminal for connection to a first conductive endodontic probe electrode able to be inserted into the root canal or one of the root canals of a tooth, a second electrode shaped to be brought into electrically conductive contact with an oral mucous membrane, one or more frequency-generating means able to produce alternating electrical signals at least two frequencies, and means for measuring the electrical magnitude of the alternating signals in a circuit comprising the frequency-generating means, the first electrode inserted into the root canal of the tooth and the second electrode in contact with the oral mucous membrane, characterised in that it has frequency selection control means for exciting the circuit at a first lower frequency and at a second higher frequency, and for respectively measuring a first level and a second level of standardised magnitude of the alternating electrical signals in the said circuit and means for detecting and/or signalling when the first level measured at the first lower frequency is not greater than the second electrical magnitude level of the alternating signal measured at the second higher frequency. According to the invention the said lower and higher frequencies are sufficiently far apart for the two respective levels to meet and become substantially equal at a point of coincidence corresponding to the position of the apex.

It appears, when consideration is given thereto, that the invention highlights a fact which was not obvious. Curiously the invention is distinctive in that the lower frequency and the higher frequency are selected so that in an initial phase, corresponding to the commencement of the insertion of the point of the endodontic probe electrode at the beginning of the root canal, the first level measured at the lower frequency is higher than the second level measured at the higher frequency.

Generally speaking, according to the invention, the lower and higher frequencies are selected in opposing frequency bands which are distinct and/or far apart, i.e. non-adjacent, or the said lower and higher frequencies are even separated by one or more orders of magnitude. The said higher frequency is preferably at least two, three or four orders of magnitude higher than the said lower frequency.

Typically the said lower frequency is selected in a low frequency band while the said higher frequency is selected in a high frequency band.

In particular, the said lower frequency and the said higher frequency are located respectively in two opposing frequency ranges on either side of a frequency range including at least the conventional number four band (band no. 4 known as VLF or hm.W.B.) which covers the frequencies of three kilohertz to thirty kilohertz (3-30 kHz).

In particular, it appears that the lower frequency is lower than 950 hertz and preferably lower than 500 hertz; while the higher frequency is higher than 9500 hertz and preferably higher than 95 kHz.

More precisely, in exemplified embodiments of the invention which are set out below, the lower frequency is in a conventional number two or lower frequency band, i.e. between 300 hertz and 30 hertz or less; while the higher frequency is in a conventional number six or a higher number frequency band, i.e. between 300 kHz and 3 MHz or even more.

According to one particular embodiment of the invention set out below, the lower frequency is in a frequency band of about ten hertz to several hundred hertz, preferably around a value of 100 hertz, while the higher frequency is selected in a frequency band of the order of one half or one megahertz to five or ten megahertz, it preferably being possible to adjust the choice of the higher frequency to a value selected among a group of several calibrated values around {0.5 MHz-1 MHz-2 MHz-5 MHz} depending on the electrolytic conditions prevailing in the root canal, in particular the presence of conductive aqueous ionic solutions such as the presence of physiological liquid or a common saline solution of sodium chloride (NaCl) or the presence of Dakin's liquid or a disinfectant solution based on sodium hypochlorite (NaClO).

In an advantageous and unexpected manner it appears, as shown by the exemplified results of the measuring procedures detailed below, that such a coincidence point detection mode in accordance with the invention makes it possible to obtain coherent apex depth measurement results in the presence of electrolytes, in particular in the presence of common aqueous ionic solutions based on sodium chloride (NaCl at ~1%, precisely 9%) as well as in the presence of disinfectant rinsing solutions usually used during dental surgery procedures such as the antiseptic sodium hypochlorite-based solutions (5% NaClO or 2.5% NaClO).

Another major advantage is that the invention makes it possible to resolve the root canals of complex teeth, i.e. it makes it possible to recognise, single out, determine or provide coherent measurement results for the depth of the canal of each root for complex teeth, such as teeth having relatively wide root canals or having bifurcations (forked, branched or bifurcated roots) or aberrations, according to the first results of studies carried out on reconstituted tooth models and specimens of actual teeth.

The selection of the defined values of the lower and higher frequencies makes it possible to refine the measurement of the point of coincidence of the amplitude levels plotted at the said frequencies (low frequency f and high frequency F) and to cause it to correspond precisely to the exact location point of the apex.

In particular, the choice of lower and higher frequencies can be modulated to optimise the measurement results, minimise measurement uncertainty and obtain the greatest precision depending on the conditions prevailing in the dental canal, in particular depending on whether the root canal is irrigated by a sodium chloride-based conductive solution ("physiological liquid") or by a sodium hypochlorite-based ionic solution ("Dakin's liquid") or depending on the configuration of the root canal.

Other advantages, features and objects of the invention will become clear on reading the description of exemplified embodiments detailed below, in view of the attached sheets of drawings, which are given by way of non-limiting example in which:

FIG. 1, already mentioned, shows a cross-sectional view of the structure of the canal of a dental root with the position of the apex at its end, as known in anatomy;

FIGS. 2A and 2B, already mentioned, schematically illustrate a direct current measurement of the resistance R between two electrodes, one connected to an endodontic probe, the other in contact with an oral mucous membrane and making it possible to locate the depth DP of the apex at the point where R=6.5 kilohms, according to a first known apex-locating principle;

FIG. 3, mentioned earlier, is a diagram showing—as a function of the insertion depth of a probe—the curves of voltage levels A and B plotted at two frequencies fa=1 kHz and fb=5 kHz as well as the course of the difference δ between these levels, which has a point of inflexion (extremum) at the site of the apex, according to another apex-locating principle used in one type of prior art device;

FIG. 4, mentioned earlier, is another diagram showing other voltage level curves $V_1$ and $V_2$ also plotted at the two frequencies f1=1 kHz, f2=5 kHz according to another apex-locating principle using the ratio of the voltages (ratio V2/V1) implemented in another type of device according to another prior art document;

Figure 7:
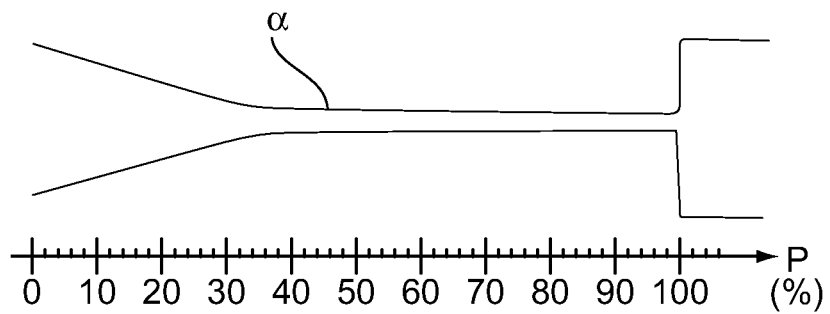
FIGS. 7, 8 and 9 show three dental root models α, β and γ (the first a narrowing in a funnel-shape with a narrow canal, the second β having a bifurcation into two root canals, the third γ having branched canal aberrations) on which depth measurements of each root canal have been trialled (cf. the following figures) with a device according to the invention.
Figure 8:
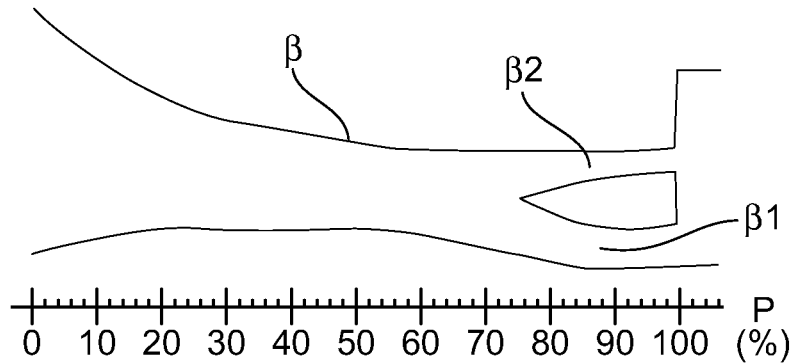
Figure 9:
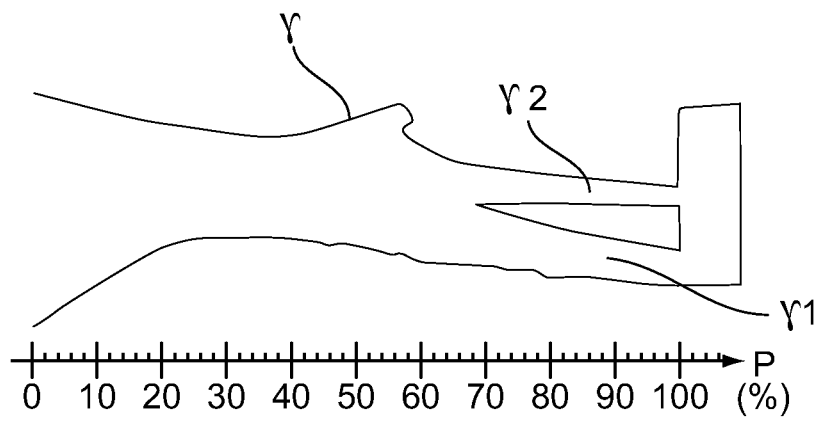
Figure 10A:
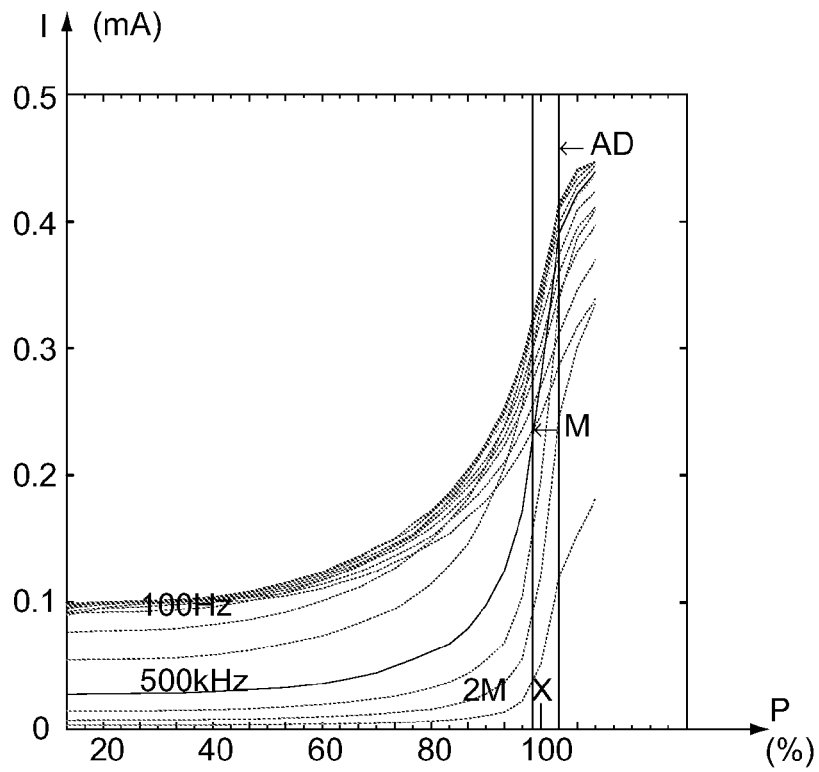
Figure 10A:
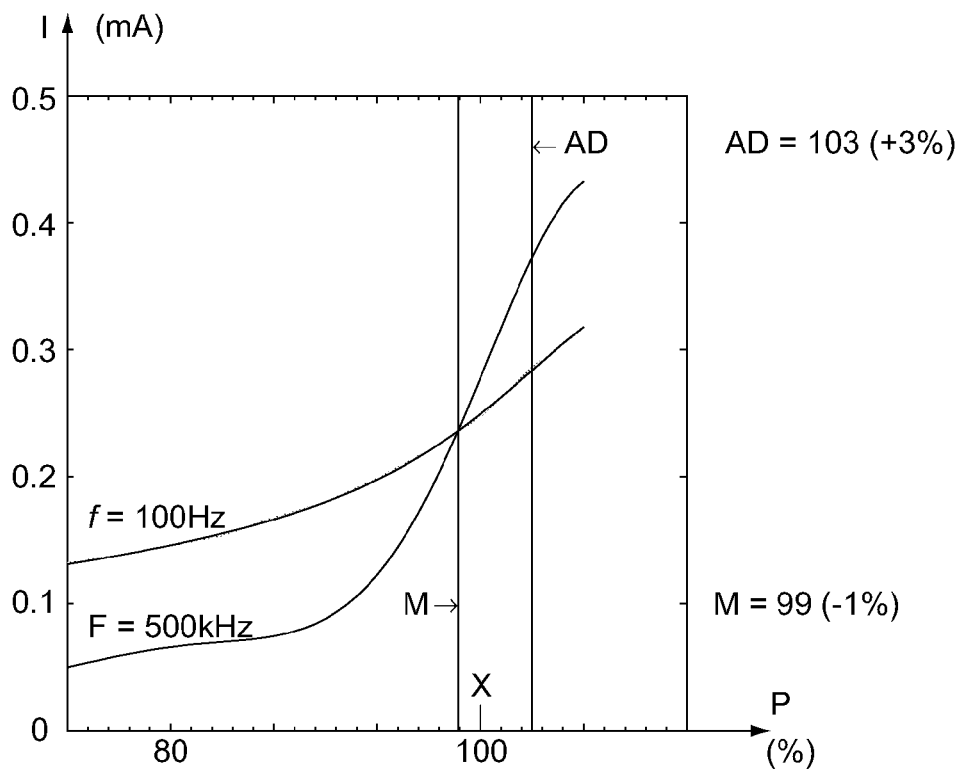
Figure 10B:
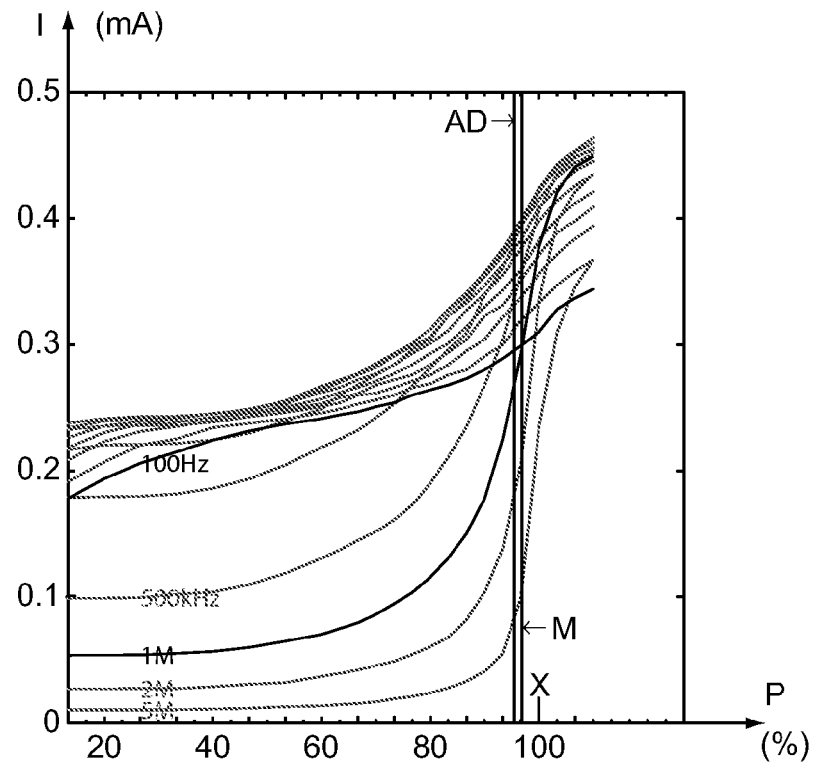
Figure 10B:
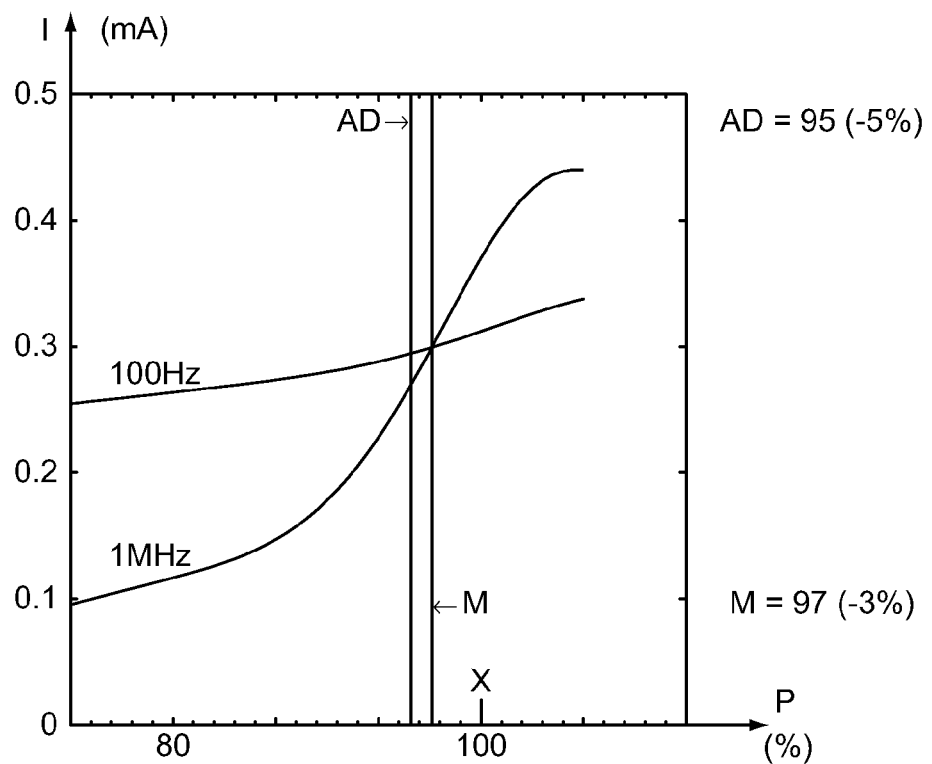
Figure 10C:
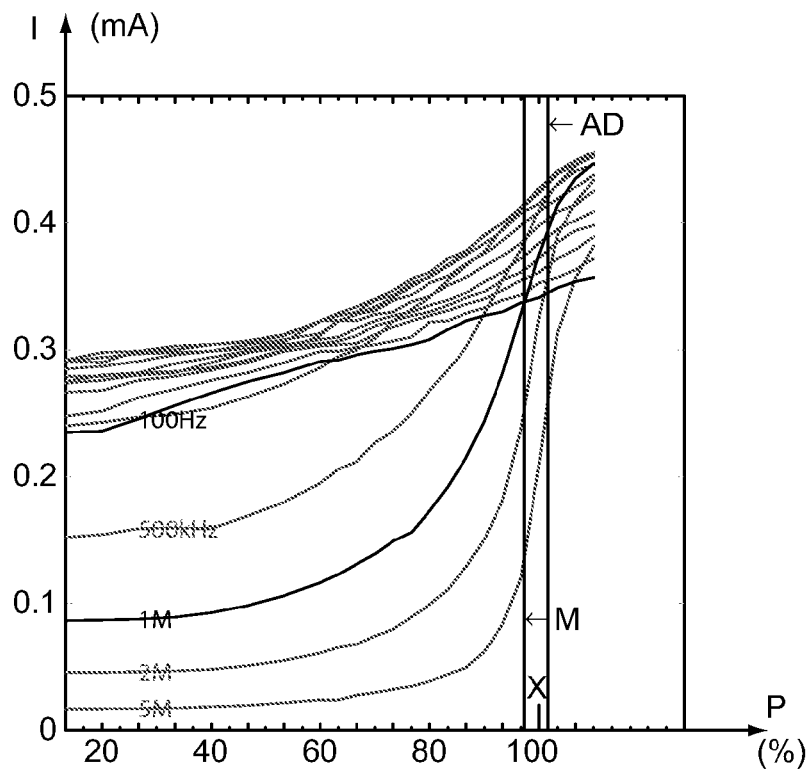
Figure 10C:
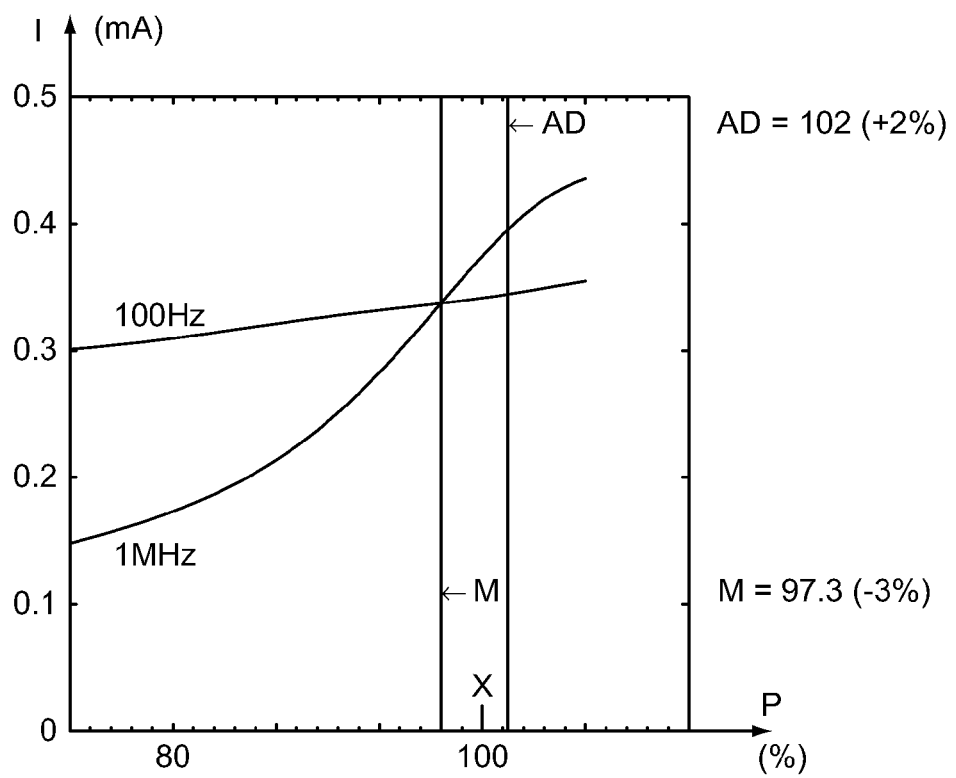
Figure 11A:
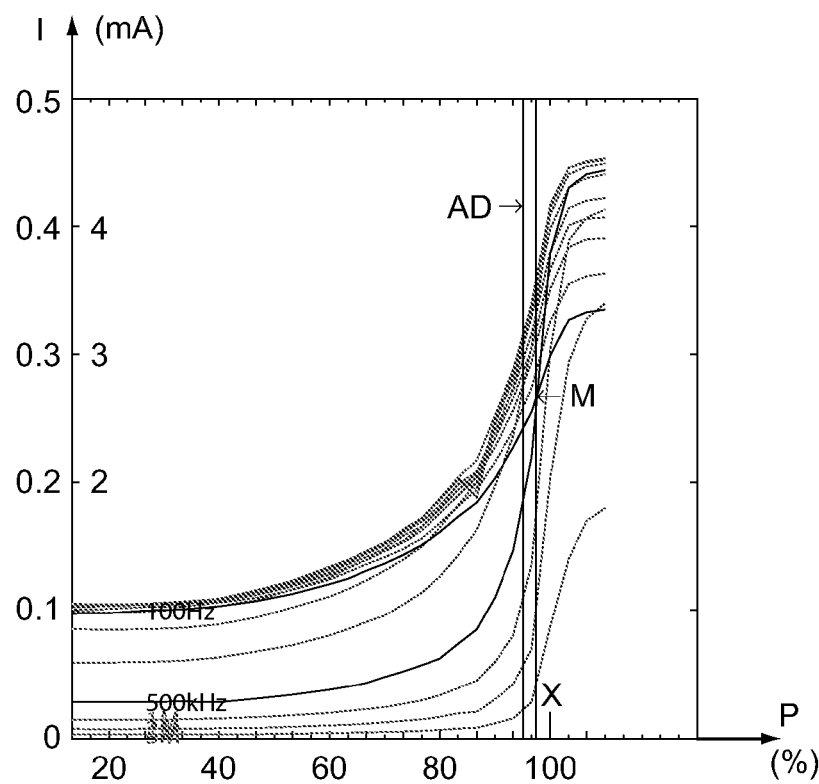
Figure 11A:
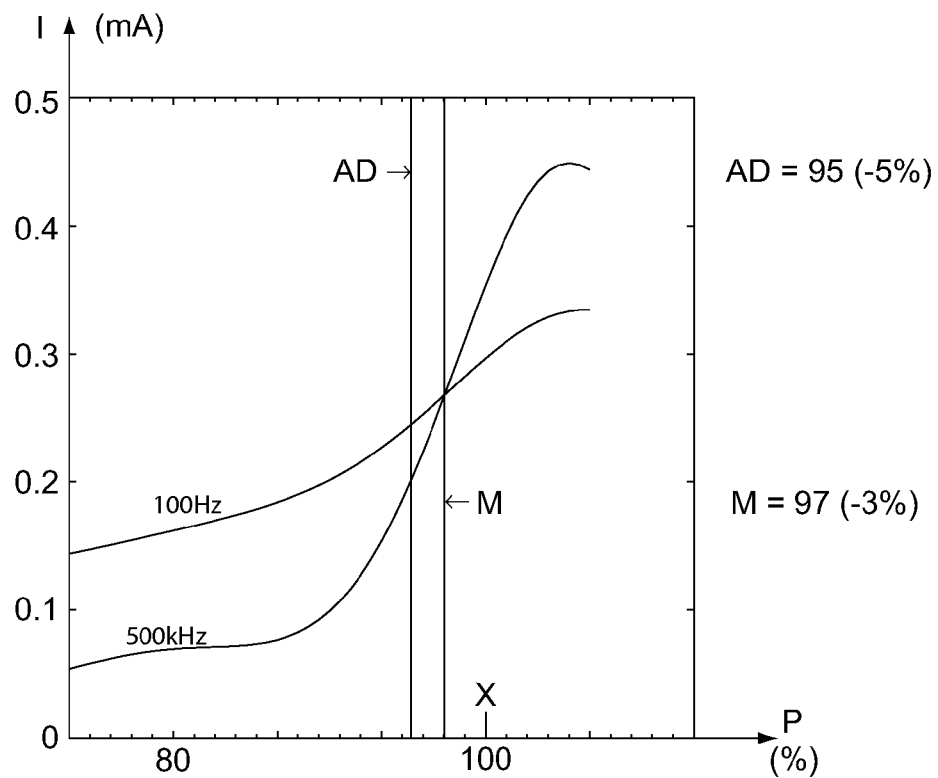
Figure 11B:
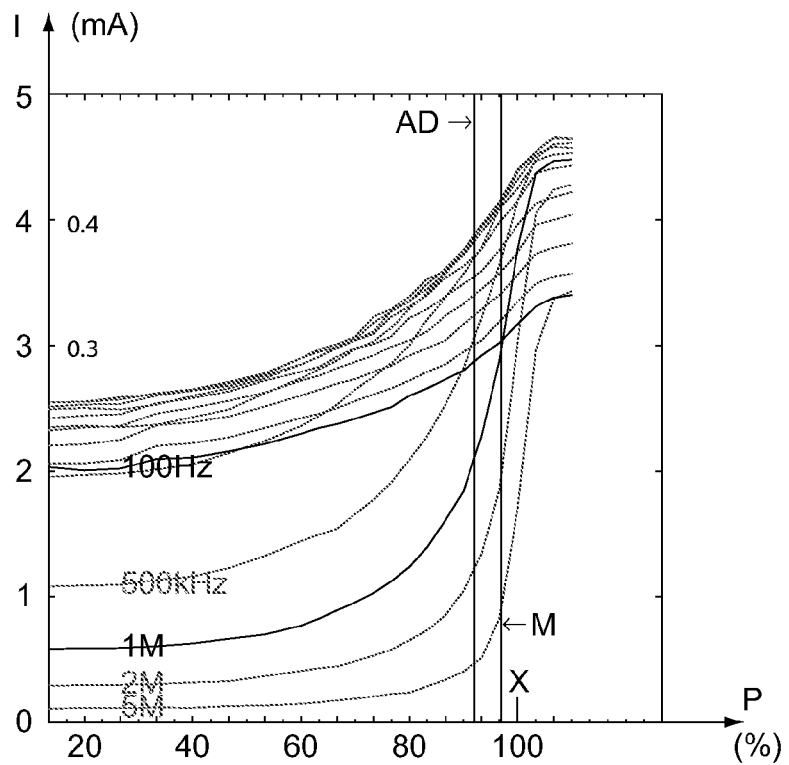
Figure 11B:
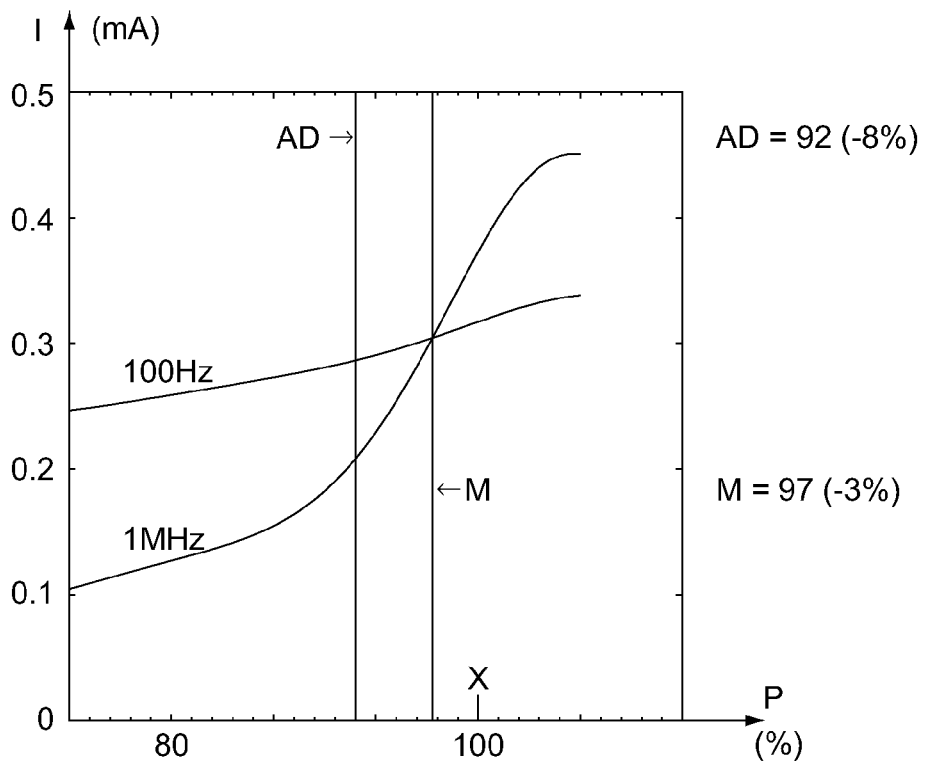
Figure 12A:
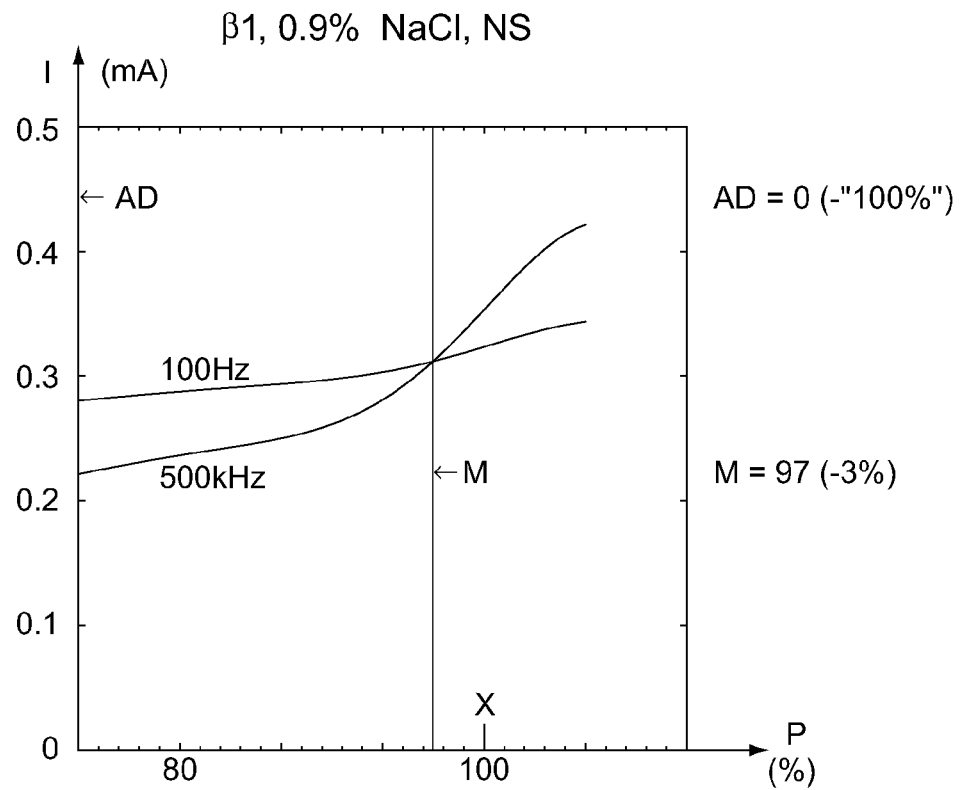
Figure 12A:
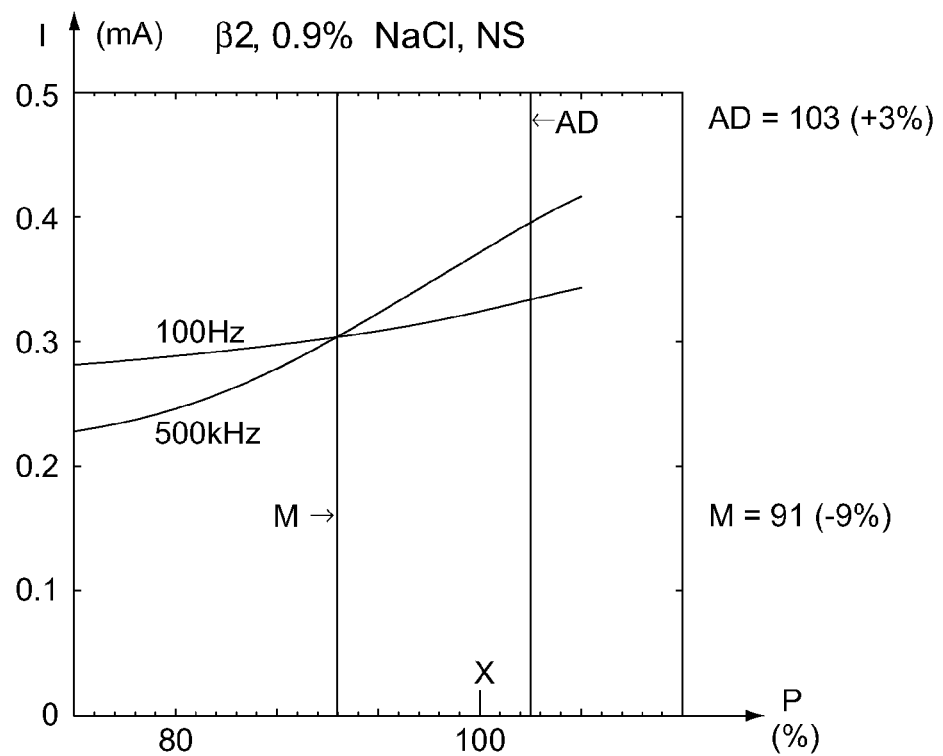
Figure 12C:
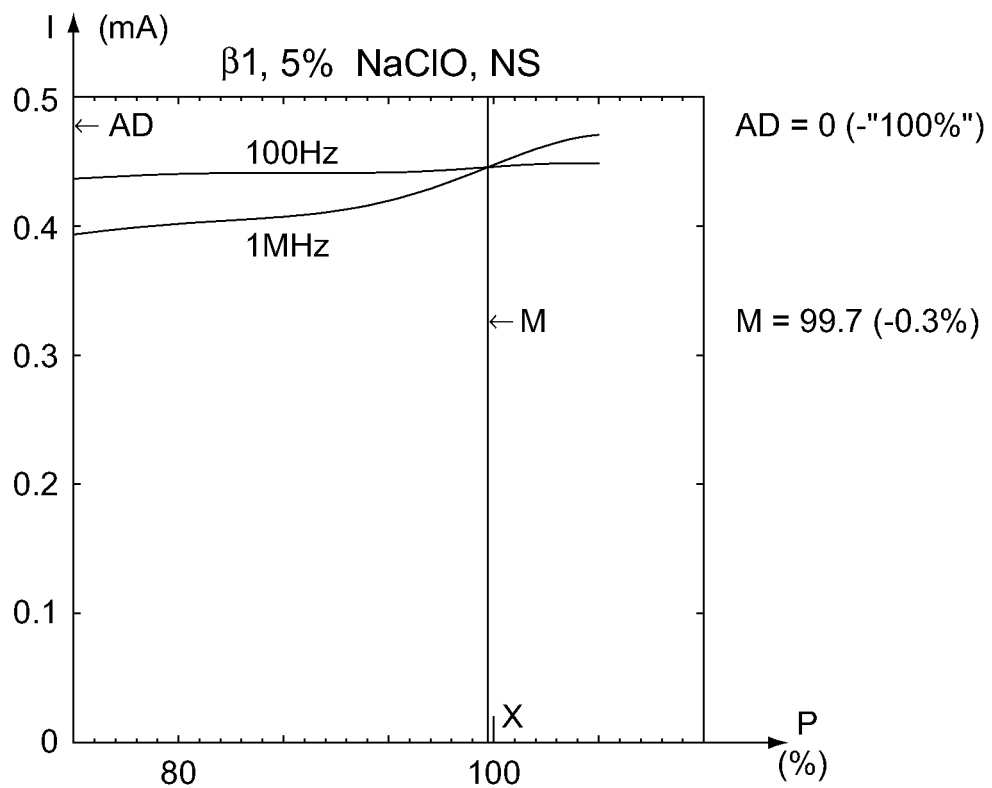
Figure 12C:
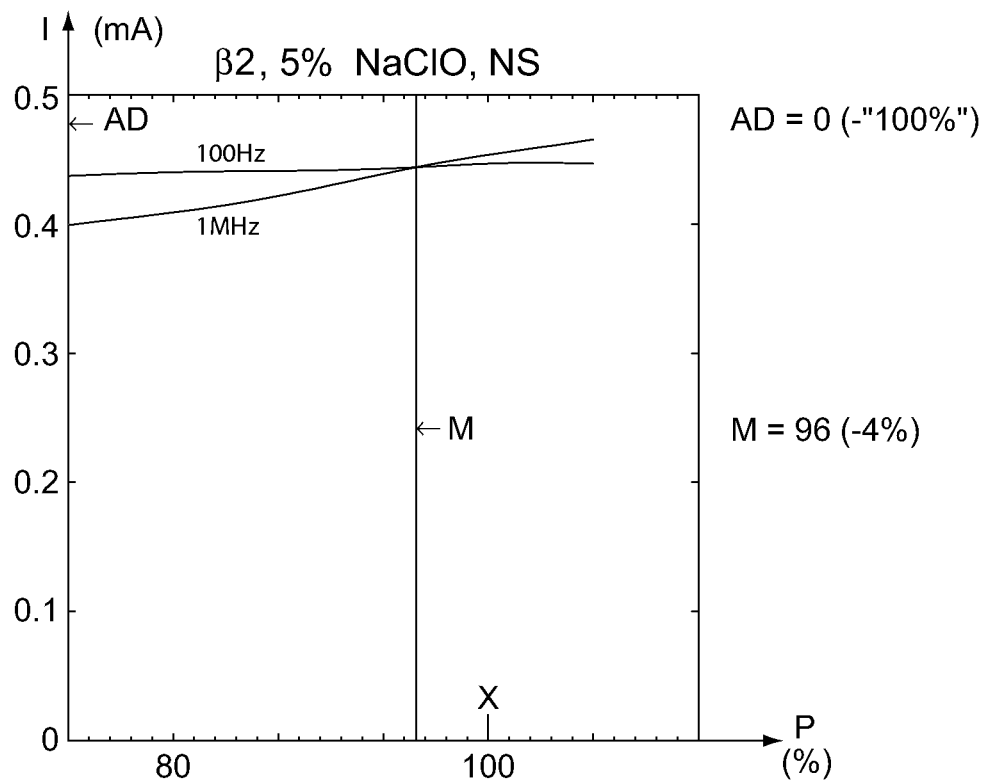
Figure 13A:
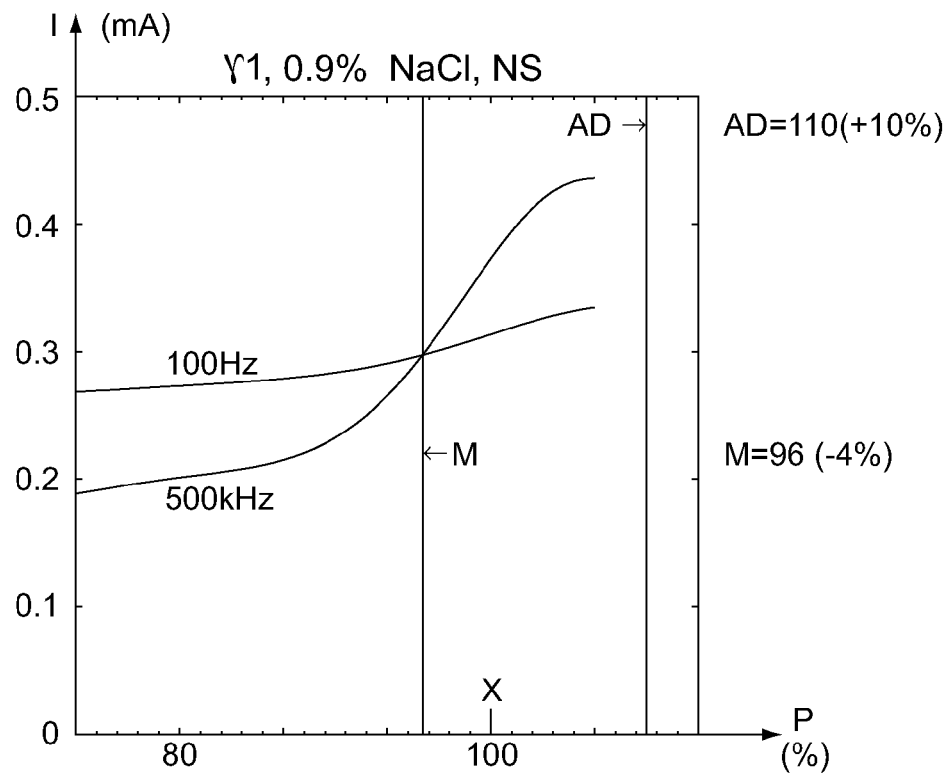
Figure 13A:
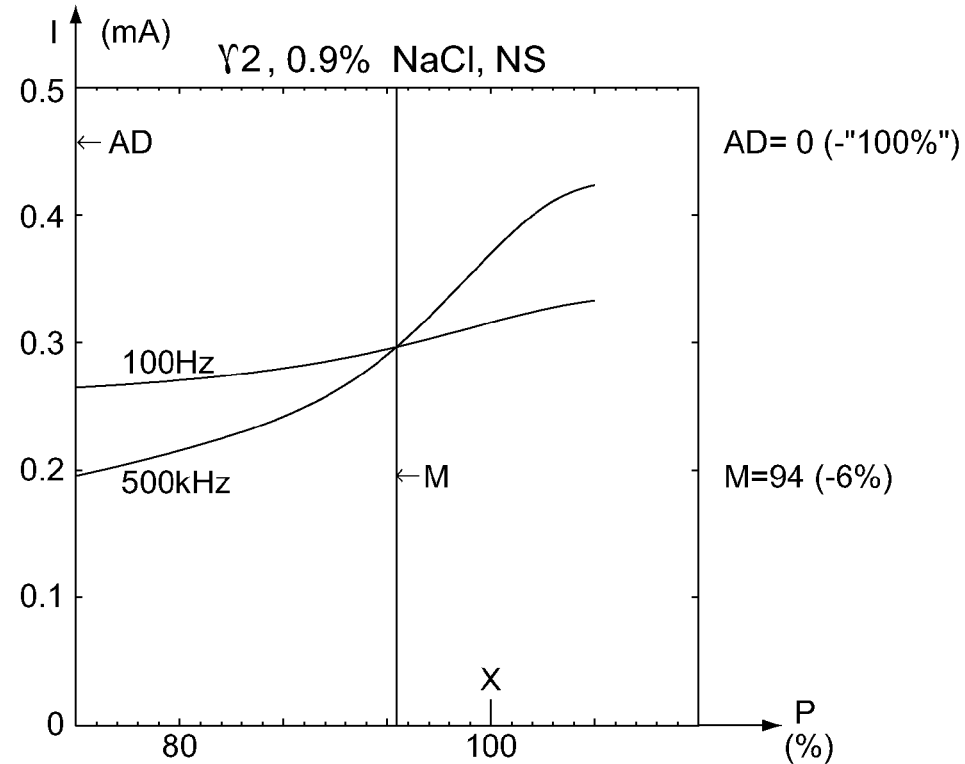
Figure 13B:
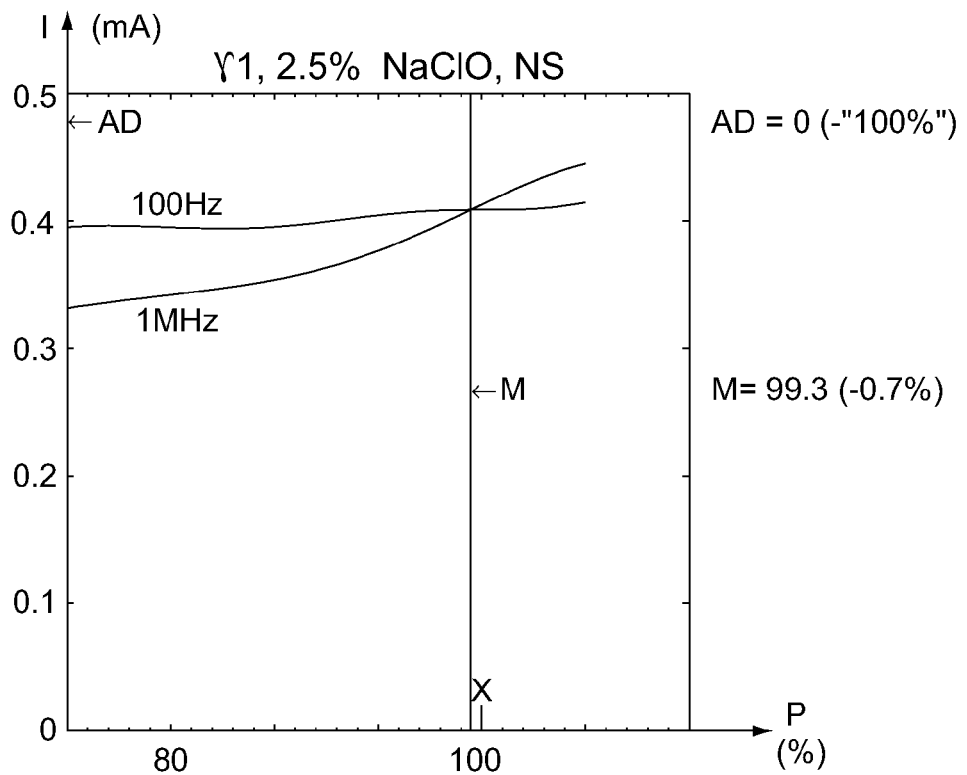
Figure 13B:
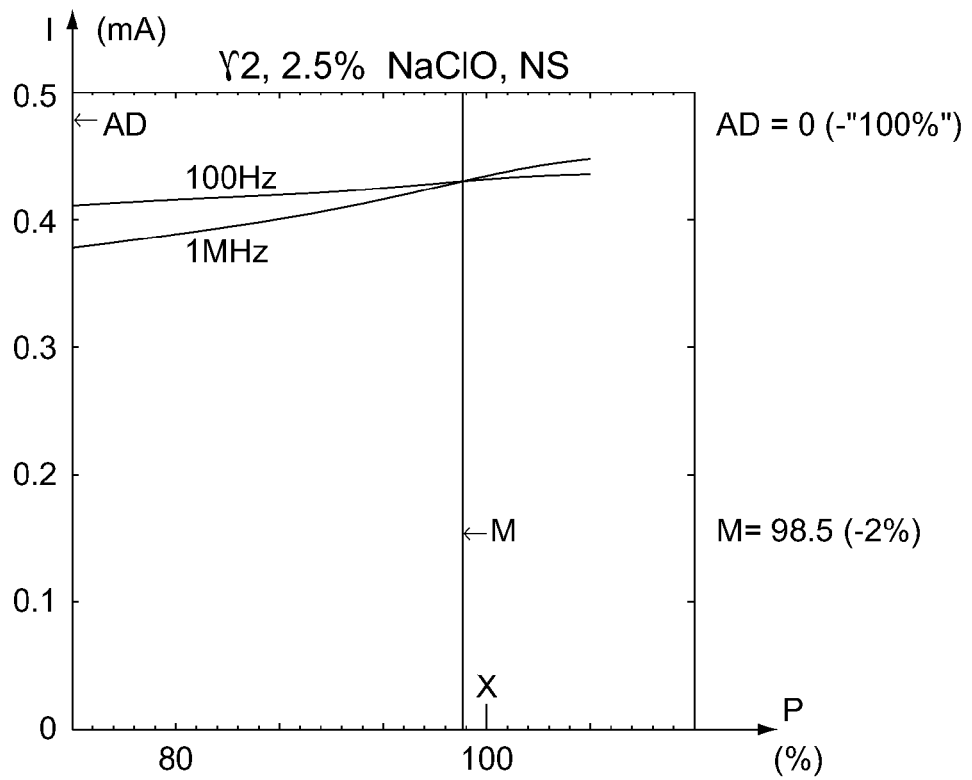
Figure 13C:
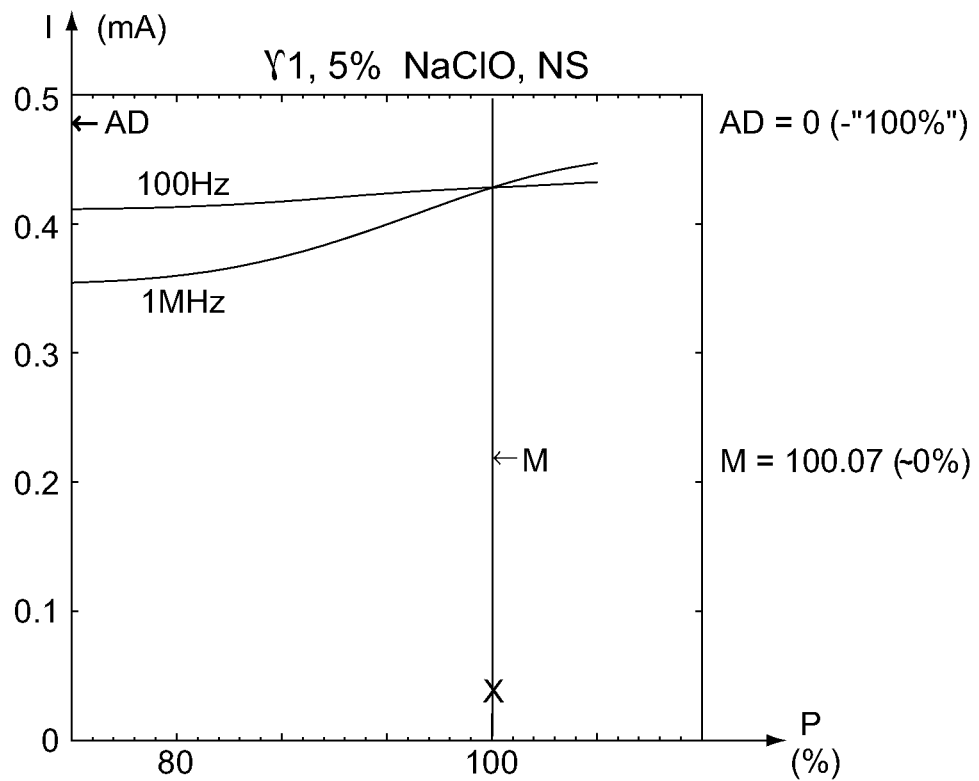
Figure 13C:
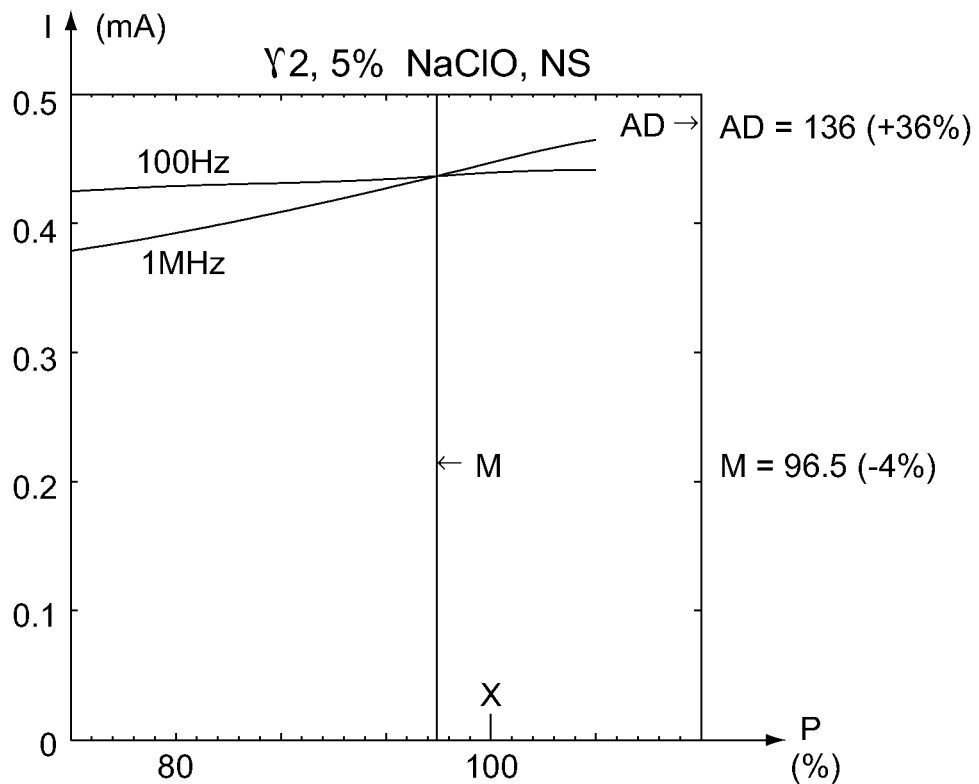
Figure 14A:
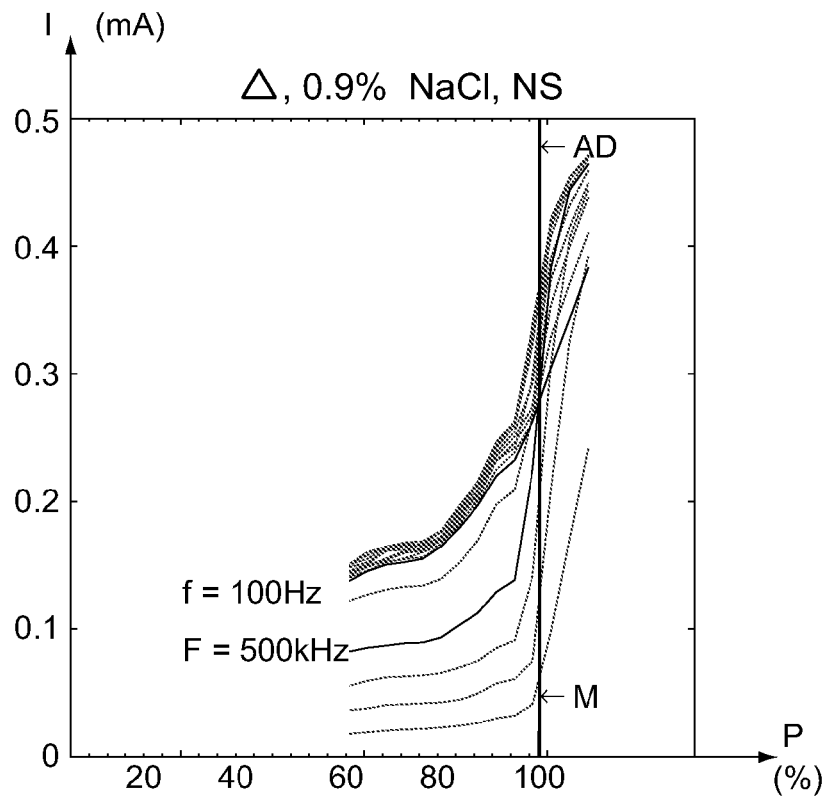
Figure 14A:
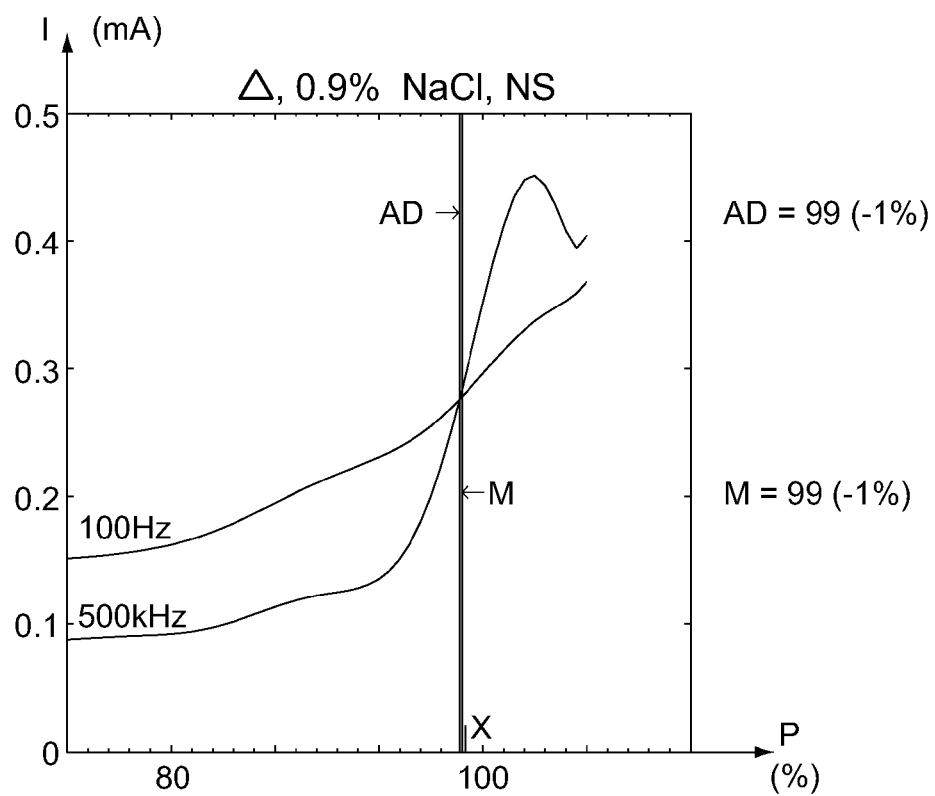
Figure 14B:
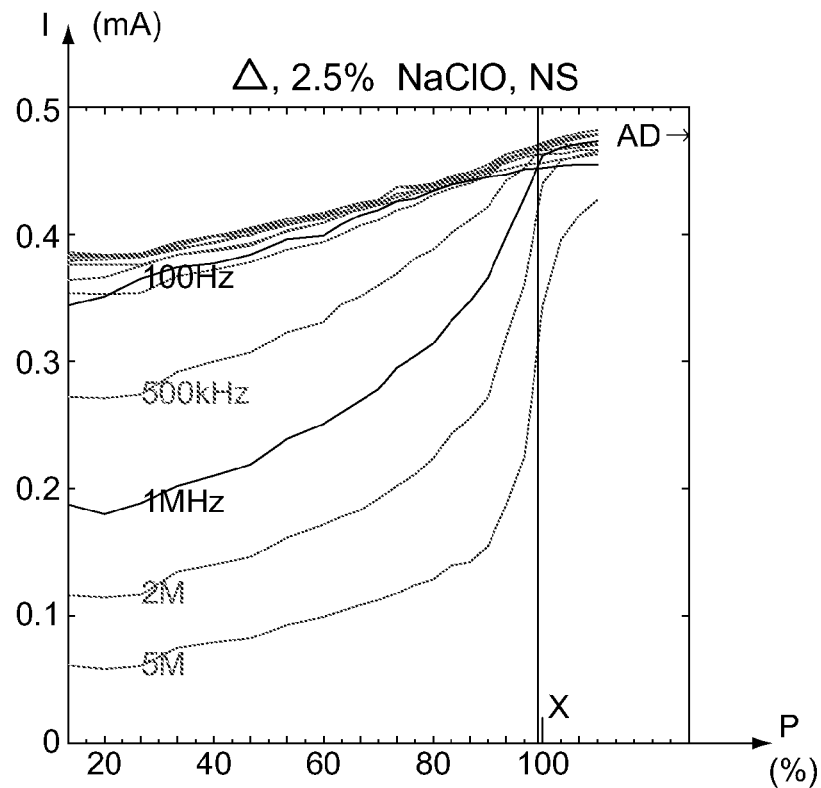
Figure 14B:
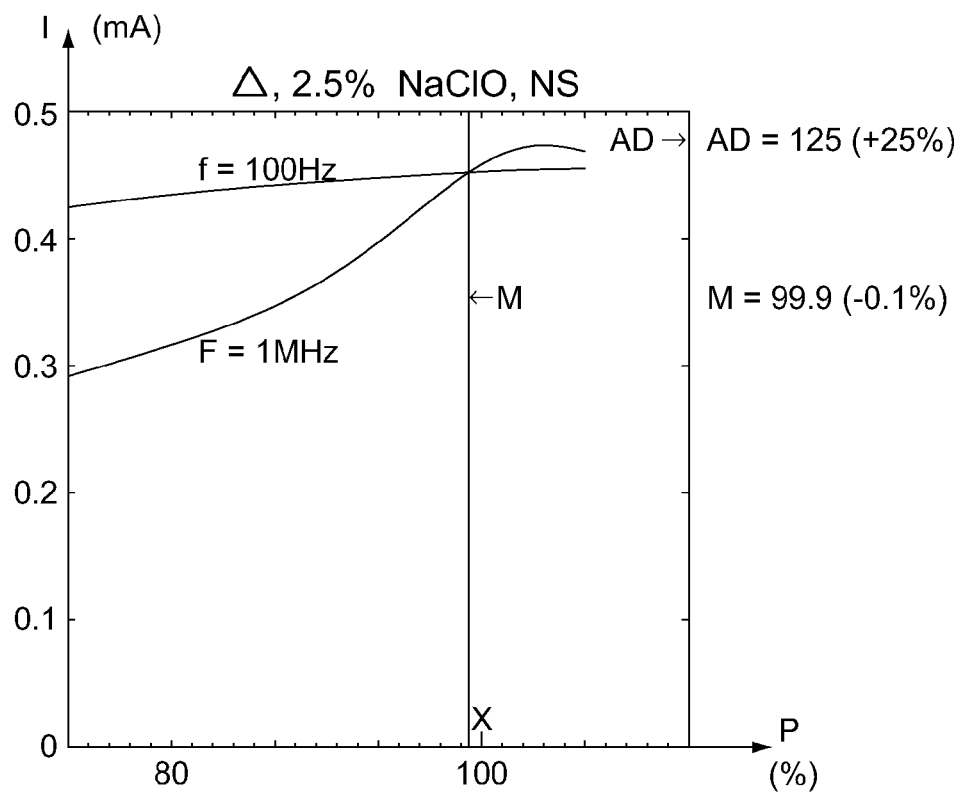
Figure 14C:
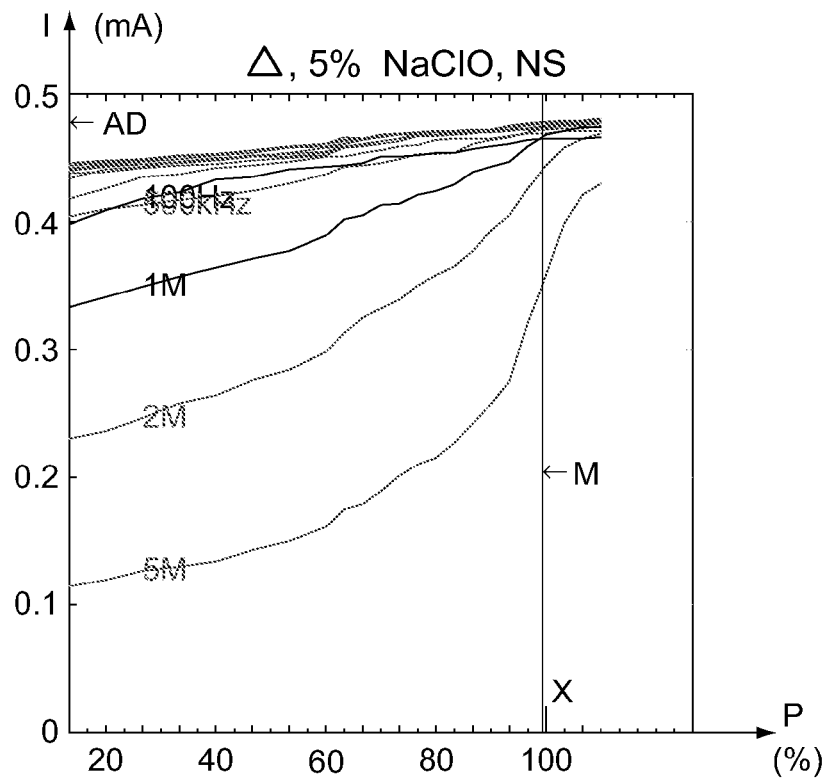
Figure 14C:
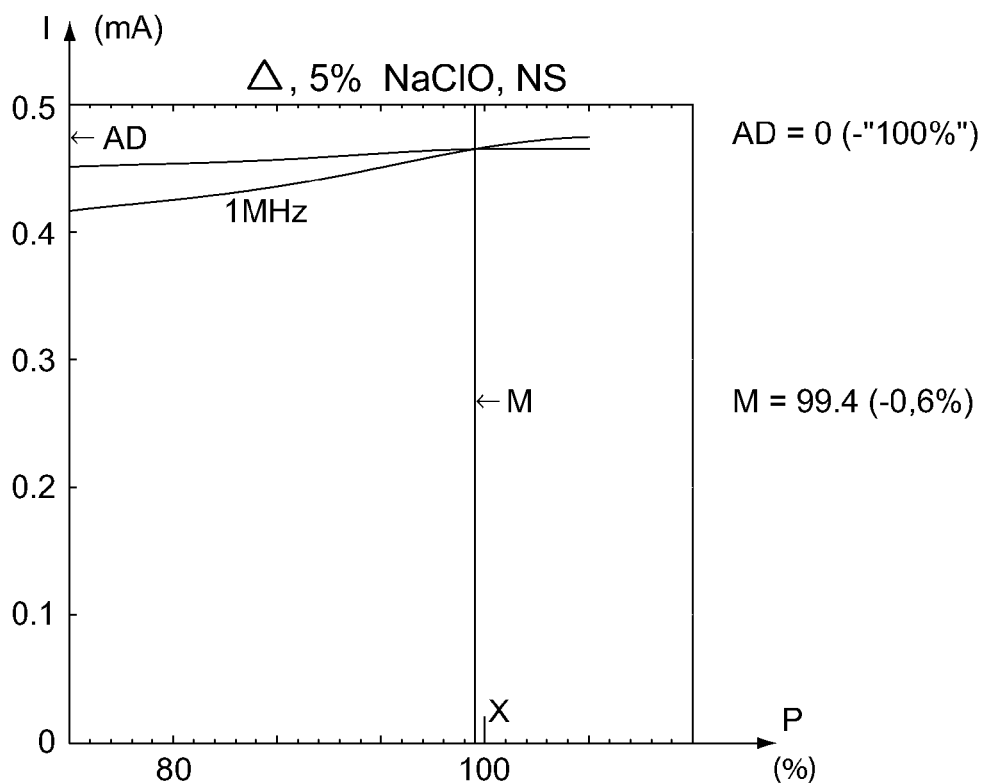
Figure 15:
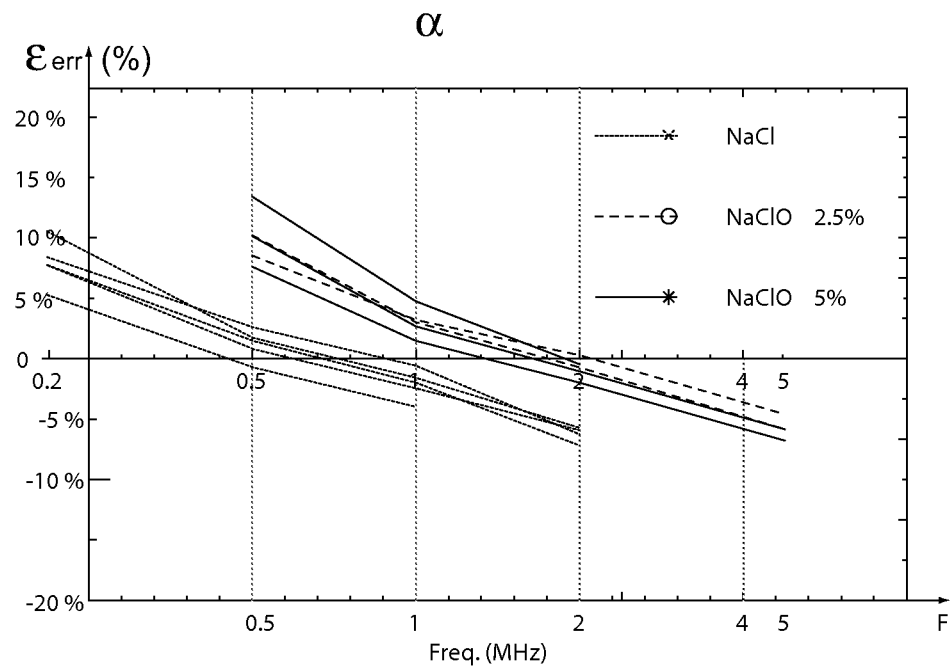
Figure 16:
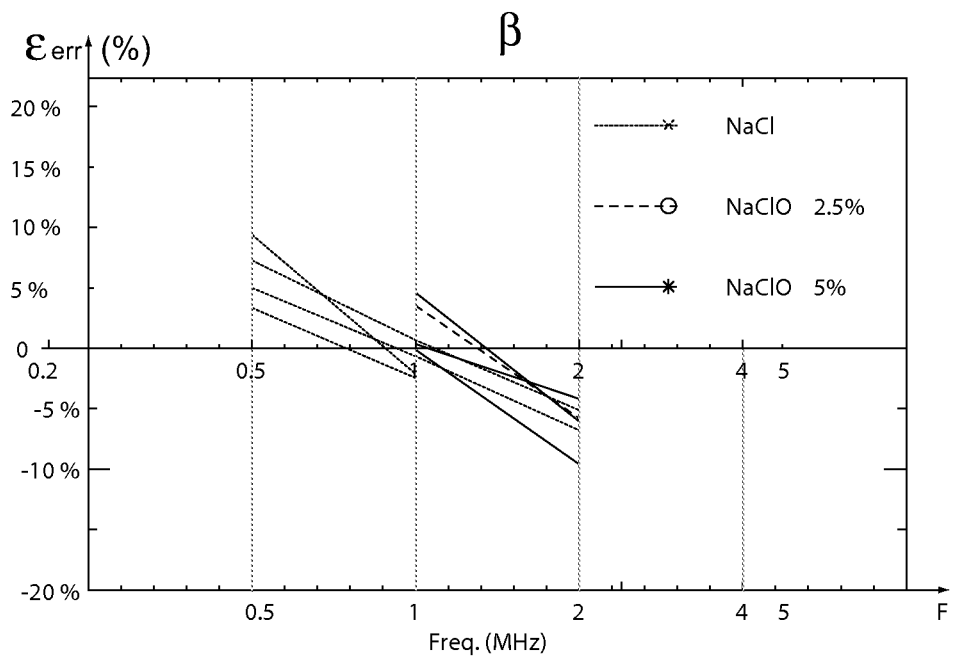
Figure 17:
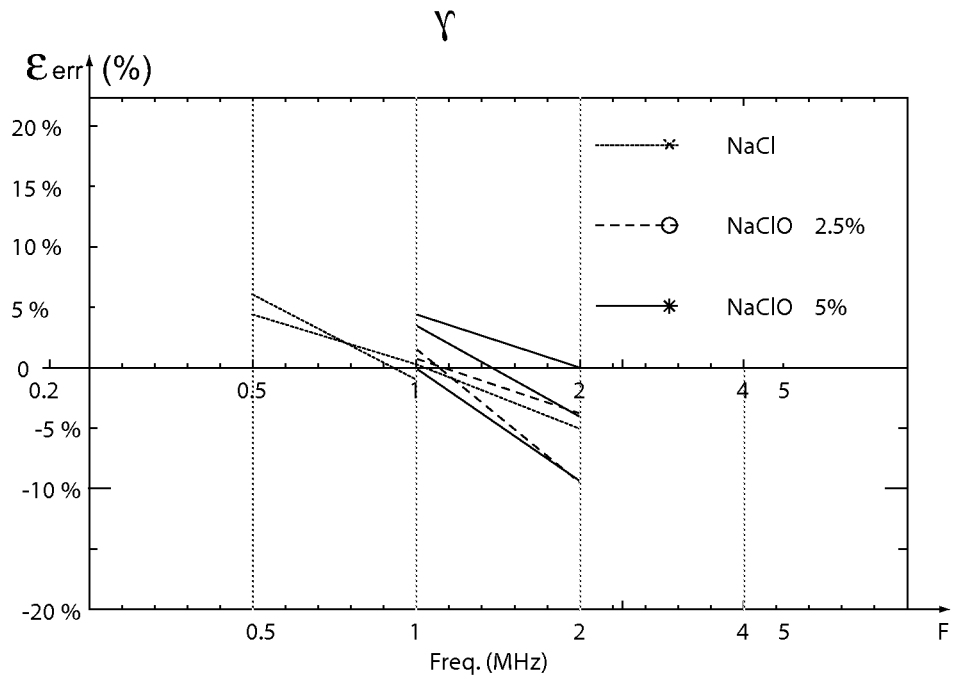
Figure 18:
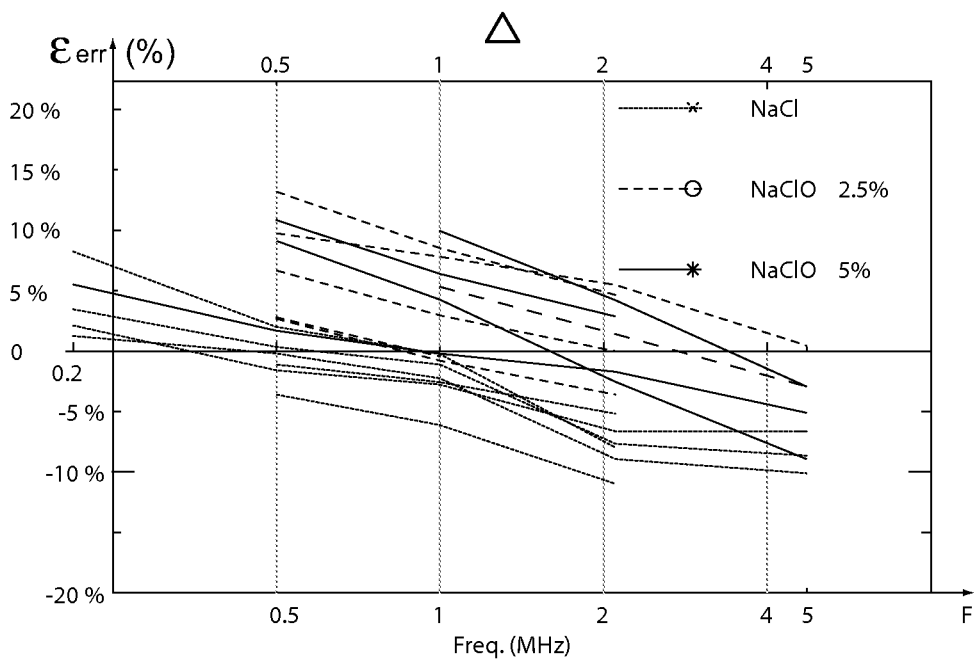

FIGS. 10A to 13'C show a series of curves showing amplitude measurement as a function of the depth of insertion of a probe electrode and plotted experimentally in relation to the three models α, β, γ of the above-mentioned root canals (FIGS. 7, 8, 9), these canals being irrigated successively with three aqueous solutions (Figure marked A: 0.9% NaCl; figure marked B: 2.5% NaClO; figure marked C: 5% NaClO) with various probes and making it possible to locate the position of the apex according to the invention;

FIGS. 10A, 10B, 10C show the amplitude/depth curves plotted in relation to the root canal model α of FIG. 7 with a bare metal probe and in the presence respectively of 0.9% NaCl solution (10A), 2.5% NaClO solution (10B) and 5% NaClO solution (10C);

FIGS. 11A and 11B show the amplitude/depth curves plotted in relation to the root canal model α of FIG. 7 with a probe covered with insulation in the presence respectively of the same solutions (FIG. 11A: 0.9% NaCl) (FIG. 11B: 2.5% NaClO);

FIGS. 12A-12'A and 12C-12'C show the amplitude/depth curves plotted alternately (12, 12') in relation to the first and second root canal β1 and β2 of the dental root model β with forked branching of FIG. 8 in the presence respectively of the same solutions (FIG. 12A-12'A: 0.9% NaCl) (FIG. 12C-12'C: 5% NaClO);

FIGS. 13A-13'A, 13B-13'B and 13C-13'C show the curves plotted alternately (13/13') in relation to the first and second root canal γ1, γ2 of the branched root model γ of FIG. 9 with a bare metal probe in the presence respectively of the same solutions (FIG. 13A-13'A: 0.9% NaCl) (FIG. 13B-13'B: 2.5% NaClO) (FIG. 13C-13'C: 5% NaClO);

FIGS. 14A, 14B and 14C show amplitude/depth curves plotted experimentally in relation to an actual tooth Δ at two frequencies f=100 Hz and F=0.5 or 1 MHz, in the presence respectively of the three irrigating solutions (FIG. 14A: 0.9% NaCl) (FIG. 14B: 2.5% NaClO) (FIG. 14C: 5% NaClO); and FIGS. 15 to 18 are diagrams showing several clusters of points giving evaluations of measurement errors $\epsilon_{err}$ as a function of the value of the higher frequency F selected during depth measurement procedures on root canals α, β, γ; the diagram of FIG. 15 brings together the evaluations of measurement error ε as a function of the higher frequency F for a whole series of depth measurements on the root canal of the dental model α of FIG. 7; FIGS. 16 and 17 bring together the evaluations of error ε as a function of the higher frequency F for the root canal models β and γ of FIGS. 8 and 9 respectively; FIG. 18 brings together the evaluations of error ε as a function of F for several series of apex depth measurements on several specimens of actual teeth.

In the present invention a conductive endodontic probe is used which may have various forms and in particular be formed by a metal rod, point or file which acts as an electrode. The probe electrode is preferably in the form of a narrow, elongate, flexible metal rod, of centimetric length (of the order of one centimeter or a fraction of a centimeter to several centimeters, not more than a decimeter, typically 2-3 cm). This rod or file with a round or other cross-sectional shape has a diameter (transverse dimension) clearly less than its length. The metal rod which acts as a terminal electrode (in electrical contact with an intermediate connection electrode and/or connected to an output terminal of the generator GF) can be covered over all or part of its length by an insulating covering as in the plots of experimental curves as reported hereinafter in relation to FIGS. 11A and 11B. It is possible, in particular, to use endodontic probes which are available through commercial networks, and the experimentation results reported hereinafter will be compared with those of an existing prior art apex-locating device, the results obtained with this prior art apex-locating device being marked by the reference AD in FIG. 10A and following.

Figure 5A:
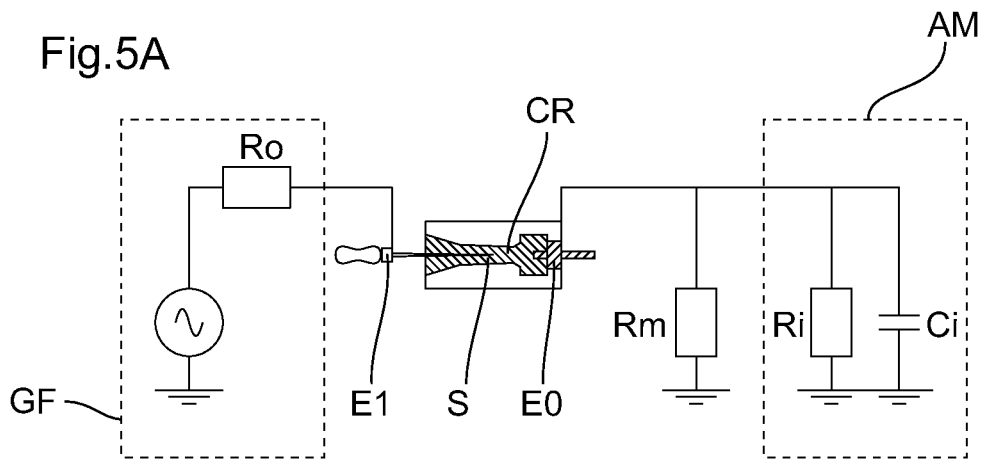
FIG. 5A illustrates a diagram of the electric circuit of the apex-locating device used according to the invention.
Figure 5B:
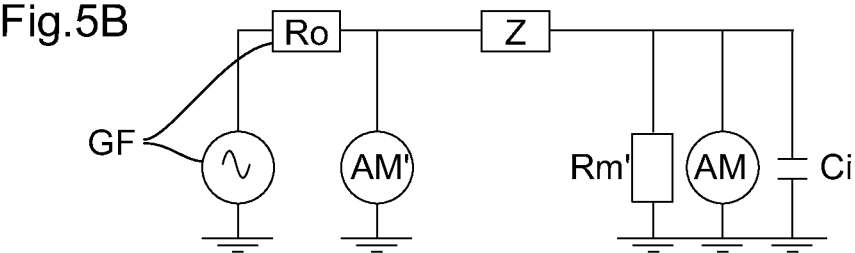
FIGS. 5B to 5D illustrate equivalent diagrams of the electric circuit of the apex-locating device according to the invention.
Figure 5C:
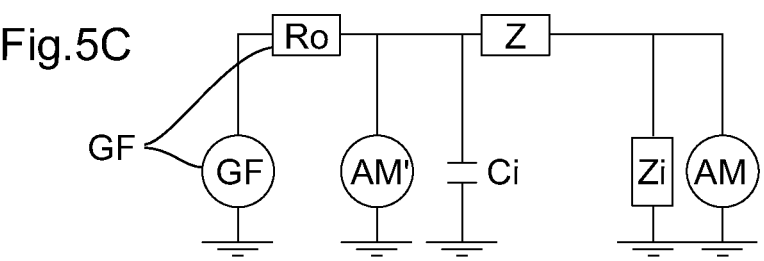
Figure 5D:
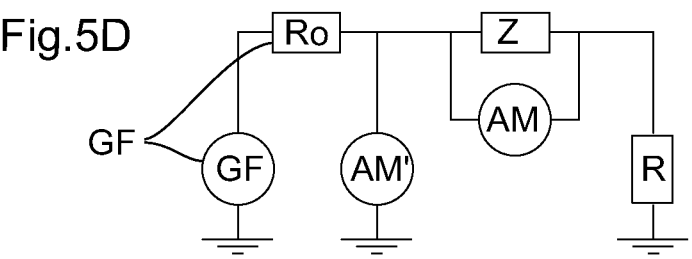

Turning to FIG. 5A, by way of reference, it appears that the electric circuit of the apex-locating device according to the invention advantageously uses a sinusoidal alternating signal frequency generator GF, connected in series with a first conductive electrode E1 which is formed by the endodontic probe S which engages in the root canal CR of a tooth specimen (hereinafter Δ) or a model of a dental canal (hereinafter α, β, γ). The circuit has a second earth electrode E0 connected in series with an assembly or apparatus AM for measuring the intensity of the alternating current which passes through the two electrodes E0-E1 and is produced by the alternating signal generator GF which is in this case a frequency-agile generator.

The measuring assembly and apparatus AM must permit measurement of the amplitude of the alternating sinusoidal signals and more precisely the amplitude of the intensity of the alternating currents. However, according to the exemplified measuring assembly of FIG. 5A the measuring apparatus AM can measure the voltage amplitude of the alternating signals, in particular the absolute amplitude (as a peak, effective or RMS value) and be connected in parallel on the terminals of a reference measuring resistor Rm placed in series with the electrodes E0-E1 and the frequency-agile generator GF of the circuit. According to a first experimental example 5B, 5C, 5D, the measuring apparatus AM can be an oscilloscope covering an extensive range of frequencies and the measuring terminals of which are connected to the terminals of a measuring resistor Rm operating at a very low value compared with the input impedance Zi of the apparatus AM, i.e. compared with its input resistance Ri and especially the capacitance Ci between its input terminals. By way of example, with an input resistance of ten megohms ($R_i$=10 MΩ) and a capacitance of fifteen picofarads ($C_i$=15 pF), a measuring resistor Rm having a value of the order of ten thousand ohms or less, for example one or several thousand ohms, makes it possible to have a high cut-off frequency, greater than one megahertz (fc>1 MHz) and even than several megahertz, even about ten megahertz (fc>10 MHz).

In an advantageous manner such a measuring impedance (i.e. $R_m//C_i$=10 kΩ//15 pF) is adapted to the intrinsic impedance Z found between the two electrodes E1 and E0, i.e. the actual impedance Z of the root canal CR.

The circuit GF or the alternating signal generating means must be suitable for producing signals with frequencies in separated frequency ranges and in particular be able to produce alternating signals at least two frequencies (f, F) selected in opposing frequency bands, i.e. in decades of frequencies which are distinct and preferably distant, i.e. separated by one or several decades or bands of frequencies. One of the two frequencies (f) is designated herein as being the first frequency, low frequency or lower frequency; the other frequency (F) is called the second, high or higher frequency. The first frequency f belongs to a domain usually considered the domain of low electrical frequencies, i.e. the domain of frequencies lower than the very low radioelectric frequencies (f<3 kHz—lower limit of the conventional number 4 radioelectric band). The first frequency f belongs, in particular, to the domain of frequencies including the band conventionally numbered 2, around $10^2$ Hz (30 Hz≦f≦300 Hz), while the second frequency F belongs to another opposing frequency domain, usually considered as the high electrical frequency domain, i.e. the domain of radiofrequencies (F>>3 kHz), a domain which includes, in particular, the band of medium radioelectric frequencies conventionally numbered 6, around $10^6$ Hz (300 kHz≦F≦3 MHz). The said number 6 frequency band, which covers a decade of frequencies around about 1 MHz, is also known in radioelectricity under the terms medium frequencies, MF, or medium wave, MW, metrically abbreviated to hm.B or hm.W for hectometric band or waves.

Consequently, the measuring apparatus must cover a wide range of frequencies covering frequency ranges including the bands ranging from frequencies lower than the very low radio frequencies or low electrical frequencies (f=30 to 300 Hz or 3000 Hz) and the medium frequency radio bands or high frequency bands (F=300 kHz to 3 MHz or more).

In the measuring circuit example of FIG. 5A, the apparatus AM measures an absolute value RMS of the amplitude of the voltage U at the terminals of this measuring resistor Rm.

Such measurements correspond to absolute amplitude measurements (RMS) of the intensity I of the current which passes through the canal between the electrodes E0-E1 and the whole circuit excited by the frequency generator GF which produces an alternating signal voltage at the defined frequency selected by its frequency selection control.

The absolute amplitude value may equally be a peak value of the alternating signal Imax, a peak to peak value 2. Imax, a calculated effective value (i.e. Imax/√2), a true effective value Ieff, a so-called RMS (root mean square of the momentary amplitude values) or other absolute value measurements, in particular values proportional to or linked to the previously stated absolute values, provided that these are standardised values giving a standard of the amplitude of the alternating signal.

Several in-depth sequential series of measuring procedures were carried out by the inventors covering frequency ranges from 100 Hz to 5 MHz, successively registering sequences of measurement curves at determined frequencies spaced apart by an exponential frequency jump (i.e. series 1, 2, 5, 10, . . . , 100, 200, 500, 1000, . . . , 500000, 1000000, $2.10^6$, $5.10^6$ . . . Hz), concentrating in particular on the course of the amplitude curves of the alternating signals plotted at these various frequency values depending on the distance of the end of the endodontic probe from the end of the root canal, obtained by varying the insertion depth of the probe within the root canal of a large number of models of dental canals and actual teeth.

Figure 6A:
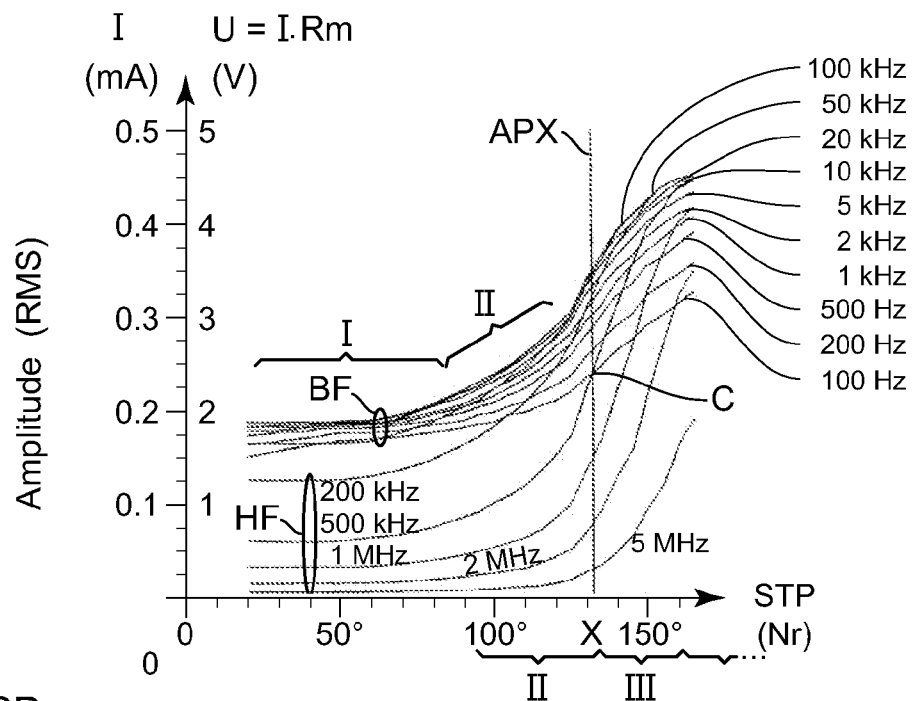
FIG. 6A is a diagram of amplitude measurement as a function of the insertion depth of the probe electrode, showing the general course of the curves plotted at different frequencies from low frequency to high frequency and their intersection according to the invention.

FIG. 6A shows the general course of a series of measurement curves thus obtained by using such a system AM for measuring the amplitude of the alternating signals produced by a frequency-agile generator GF in a series circuit comprising the two conductive electrodes E0-E1, the endodontic probe electrode E1-S being engaged in a root canal CR (dental canal model or specimen of an actual tooth). Each measurement curve is plotted at a defined frequency. The curve brings together a group of measurement points at the said frequency depending on the depth of insertion reached by the end of the probe. The measurement points are plotted by pressing the probe step-by-step deeper STP into the root canal. The insertion of the probe is effected on a micromechanical bench with micrometric displacement, the obtained stepping and the obtained positioning precision of which are clearly less than one millimeter and of the order of about a hundred micrometers or less. At each step STP, the absolute amplitude (RMS) of the alternating signal is measured at the selected frequency at the terminals of the measuring resistor Rm.

Each curve of FIG. 6A brings together these measurement points of the absolute amplitude level of the intensity I (I=U/Rm) depending on the depth STP or P of insertion of the end of the conductive electrode E1 formed by the endodontic probe S into the root canal CR, the probe being displaced step-by-step STP by the micromechanism.

As can be seen on each curve of FIG. 6A and the following FIGS. 6B and 10A-14C, it appears that each group of more than about a hundred measurement points determined at a defined frequency forms a group of measurements which is totally coherent and continuous, forming a smooth, regular curve with no discontinuity.

In a general way, according to the overall course of the amplitude measurement curves of FIGS. 6A-6B and following 10A-14C it will be observed that each curve has at least three portions I, II, III, . . . as follows:

a first portion I in which the amplitude level of the alternating signals is stable at a base level or increases very slightly with the depth of insertion P of the probe; this first portion I corresponds to the initial phase of insertion of the probe at the start of the dental canal and extends to the whole phase where the end of the probe runs over the major part of the length of the root canal, i.e. from the introduction of the probe into the tooth crown (crown-like part) as far as the apical zone II;

a second portion II in which the amplitude level (RMS) of the signals increases rapidly according to the depth of insertion of the probe; as indicated by a vertical axis line APX in FIG. 6A or an upright marker X of depth P in the following FIGS. 6B and 10A-14C, this second portion II corresponds to the phase in which the end of the probe crosses the apical zone around the position of the apex APX;

a third portion III, if applicable, in which the amplitude level of the alternating signals increases less rapidly and/or no longer increases with the depth P of insertion of the probe, so that the amplitude level is re-established and possibly stabilises at a terminal upper level; this latter portion III corresponds to a phase where the end of the probe has passed the apical zone and is embedded at depth beyond the position X of the apex APX; the signal level varies little or no longer varies with respect to the terminal upper level.

As shown in FIG. 6A in the curves plotted at the low frequencies (designated by "BF"), i.e. at the first lower frequency values of, for example, 100 Hz, 200 Hz, 500 Hz, . . . , 10 kHz, 20 kHz, 50 kHz etc., it is observed that each amplitude level curve increases moderately between a relatively high initial base level in the region of I=0.15 to 0.2 mA, to reach a final upper level between I=0.3 and 0.45 mA.

In fact a number of bundles of curves can be distinguished, in particular a first bundle BF of low frequency curves (i.e. 100 Hz, 200 Hz, 500 Hz, . . . , 10 kHz, 20 kHz, 50 kHz) and another bundle HF bringing together curves plotted at high frequency (i.e. . . . 200 kHz, 500 kHz, 1 MHz, 2 MHz, 5 MHz, . . . ). Among the first bundle BF of low frequency amplitude curves, the curve produced at the first lower frequency value f=100 Hz seems to have the lowest amplitude level variation between an average initial base level I1≈0.15 mA and a terminal upper level I3 ≈0.325 mA. In the other bundle HF of high frequency HF amplitude curves the curves are stepped regularly by levels decreasing with the increase in their measurement frequency F. The curve produced at the greatest higher frequency value F=5 MHz shows both a minimum initial base level and a minimum terminal upper level. Among this bundle of high frequency HF curves, the curves produced at the intermediate high frequency values F=500 kHz, 1 MHz, 2 MHz appear to be those undergoing the greatest amplitude level variation, between a particularly low initial base level and a particularly high terminal upper level.

However, as suggested by FIGS. 6A-6B and FIGS. 10A-14C, the levels of these curves fluctuate and vary depending on various parameters, such as the type of tooth specimen, the geometric configuration of the root canal(s) (wide, narrow, branches and/or aberrations), the presence of electrolytic media (physiological liquids, diluted ionic solutes based on NaCl or NaClO) and, most of all, the frequency and choice of particular frequencies according to the invention.

During these measurement procedures the inventors concentrated on cumulative plots of synthetic curves of amplitude measurement, the measurements relating to the absolute amplitude of the intensity I of the alternating signals as measured at the terminals of the measuring resistor Rm in series with the electrodes E0-E1, the curves being produced according to the depth of insertion of the endodontic probe electrode S and according to the value of each of the selected frequencies. In these systematic study procedures the inventors used a frequency-agile alternating signal generator GF covering frequency bands ranging from the conventional number two band (corresponding to the band around $10^2$ Hz or 30 to 300 hertz) to the conventional number six and seven bands (corresponding to the band around $10^6$ Hz, i.e. 300 kHz to 3 MHz, and to the $10^7$ Hz band, i.e. 3 MHz to 30 MHz).

From among all these series of curves the inventors selected certain ones of the curves produced at defined frequencies located at the ends of the frequency spectrum of the broad frequency ranges covered by the generator, and noticed that these selected curves, produced at particular opposing frequencies, have the characteristic of intersecting.

Figure 6B:
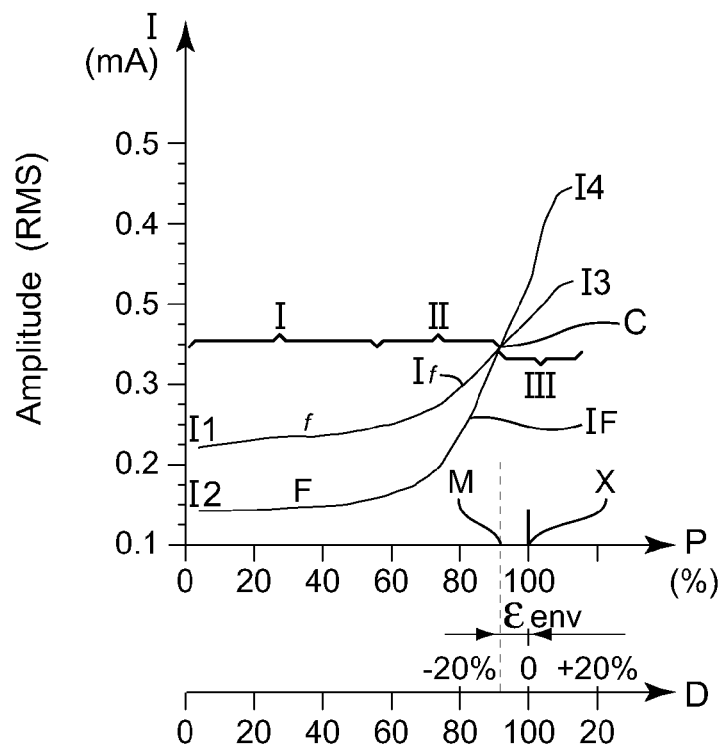
FIG. 6B shows a diagram of curves drawn from FIG. 6A, showing the intersecting of two particular selected measurement curves plotted at two opposing frequencies, one at low frequency f=100 Hz, the other at high frequency F=500 kHz, their point of intersection C corresponding to the position X of the apex according to the invention.

More precisely, the diagram of FIG. 6B shows a selection of certain particular curves of FIG. 6A, the two selected curves being plotted at two defined frequencies f and F belonging to the opposing frequency bands at the ends of the frequency spectrum of the alternating signal generator GF. The two curves f and F of the diagram 6B show the course of the development of the absolute amplitude levels RMS (in intensity I or in voltage V=Rm. I) depending on the depth P of the end of the probe S in the canal of a dental root CR.

In detail, in the curves shown in FIG. 6B, it can be seen that each curve has a number of zones I, II, III, . . . corresponding to the two or three portions of the dental canal in which the amplitude levels of these signals are organized into a hierarchy as follows:

in a first zone I, corresponding to the start of the introduction of the probe at the crown-like part of the tooth (crown) then to the engagement and passage over the major part of the length of the root canal, the amplitude levels I1 and I2 plotted at the two frequencies f=100 Hz and F=500 kHz vary little according to the depth (the depth P varies in this case between 0 and 1 to 3 centimeters, the distance D with respect to the apex X varying in a complementary manner between 10-20 millimeters and 0 mm). In this first zone I the first amplitude level I1 plotted at the first lower frequency (f=100 Hz) is clearly higher that the second amplitude level I2 of the intensity I or the voltage U of the alternating signal plotted at the second higher frequency (F=500 kHz);

in a second zone II, when the end of the probe reaches insertion depths P between 10 and 20 mm, corresponding to the terminal part of the root canal CR and to the approach of the apex APX (positioned at the value P=100% i.e. D=0), the two absolute amplitude levels If and IF (RMS I=V/$R_m$) of the alternating signals plotted at these two frequencies, the low frequency f and the high frequency F (in this case f=100 Hz and F=500 kHz), increase rapidly with the increase in the insertion depth P of the probe S and the decrease in the distance D with respect to the apex APX, X.

More precisely in this second zone II corresponding to the end of the root canal CR, the first amplitude level If determined at the first low frequency (f=100 Hz) has a positive rate of increase (I3−I1/ΔP) depending on the insertion depth P of the probe electrode but lower than the rate of increase (I4−I2/ΔP) of the second amplitude level IF plotted at the second high frequency (F=500 kHz), to such a degree that the second level IF determined at the second high frequency (F=500 kHz) comes closer to, catches up with, and meets the first level If determined at the first low frequency (f=100 Hz), to the point of becoming substantially equal to it and intersecting with it C.

Subsequently after this point of coincidence or intersection C, in a third zone III, the second level IF of amplitude RMS of the alternating signal determined at the second high frequency (F=500 kHz) continues to increase with a rate of increase (ΔIF/ΔP) greater than, or at least substantially equal to, that (ΔIf/ΔP) of the first signal amplitude level If plotted at the first low frequency (f=100 Hz).

Thus beyond this point C where the two levels If and IF meet and/or intersect, in the final zone, the second amplitude level IF plotted at the second frequency (F=500 kHz) continues to increase with a higher rate of increase and to move away from the first amplitude level If plotted at the first low frequency (f=100 Hz) or maintains the deviation with a rate of increase substantially equal to the first amplitude level If before they stabilise at levels IF=I4 and If=I3 which hardly vary.

According to the inventors' studies it unexpectedly turns out that the point C where there is a meeting and/or intersection of the two absolute amplitude level curves If and IF of the signals (I or V/Rm), determined in this case at f=100 Hz and F=500 kHz, is located at a depth M which apparently corresponds to the depth X of the apex APX (P=100%).

It remains that the important object during dental surgery procedures, such as a cleaning and shaping procedure of the endodontic canal, and the actual functional aim of the apex-locating systems is to not pass the apex APX and to avoid engaging beyond the apical foramen FA but to approach it as closely as possible while not reaching the apical terminus APX. Consequently, provision is simply made according to the invention to detect such a point of coincidence C where there is a meeting of, and equalisation between, the two amplitude levels If and IF of the alternating signals plotted at opposing frequencies f and F selected in the bands VLF/LF (very low frequencies/low frequencies) and MF/HF (medium frequencies/high frequencies) of the frequency spectrum of the frequency generator circuit GF. Thus by means of the invention it is advantageously possible not to pass the said point C and to avoid engaging in the third zone III in which the hierarchy of the first level If and of the second level IF is inverted and where the second level IF→I4 becomes greater and moves further and further away from the first level If→I3 (divergence of the second level IF above the first level If of amplitude RMS at the depths P>100% beyond the position X of the apex APX).

The first advantage of the invention is that the detection of such a point of coincidence C constitutes by itself an absolute measurement criterion for the position of the apex. The detection of this point of coincidence C does not make reference to a threshold and does not require a relative reference threshold to be adjusted or rated. The detection of the point of coincidence C according to the invention advantageously permits an absolute determination of the position of the apex.

According to the invention there is no need to seek to confirm that the two levels do intersect by seeking the third zone III in which the second level IF becomes higher than the first If and/or they become separate again (zone III where If→I3 and IF→I4 again become clearly distant). According to the invention it will suffice simply to detect the point C where the two levels If and IF meet and become substantially equal in order to locate the apex APX, avoiding passing this point of coincidence C as a precautionary measure.

Thus in its principle the invention provides for implementation of a method for locating the apex at the end of the root or of one of the roots of a tooth, a method intended more precisely to locate the apical constriction at the bottom of each root canal of the tooth and to determine the depth position of the apical terminus at the end of the root canal, the apex-locating method using a device comprising a first conductive endodontic probe electrode able to be inserted into the root canal of the tooth, a second conductive electrode shaped to be brought into electrically conductive contact with an oral mucous membrane, a circuit or frequency-generating means able to produce alternating electrical signals at a number of frequencies (at least two frequencies: a lower frequency, low frequency, and a higher frequency, high frequency), and means for measuring the magnitude of the alternating electrical signals produced in an electric circuit comprising the said frequency-generating means, the first electrode inserted into the root canal, the second electrode in contact with the oral mucous membrane and the measuring means, the method comprising steps consisting of:

exciting the circuit and measuring the level of magnitude of the alternating electrical signals in the circuit, respectively at a lower frequency f and at a higher frequency F (selected so that the first level If determined at the lower frequency f (low frequency) is initially (If=I1) higher than the second level IF=I2 determined at the higher frequency F (high frequency));

detecting a point of coincidence C where the two respective levels If and IF of the electrical magnitude (Amplitude RMS I) measured at the said lower f and higher F frequencies meet and are substantially equal, the said lower and higher frequencies being sufficiently far apart for such a point of coincidence C to exist, the said point C/M corresponding to the position X of the apex.

The existence of this point of coincidence C, which at first sight makes it possible to characterise a measurement of depth of the position X of the apical constriction, according to the preliminary study by the inventors, demanded more in-depth investigation by a programme of more intensive study extending to different root canal models and a series of actual tooth specimens.

An extensive programme of systematic experimental measurements of absolute amplitude level curves for the intensity of the alternating signal as a function of the depth of insertion of the probe electrode and the frequencies chosen was carried out to refine the results. This systematic study programme was carried out with adaptive probes by comparing the results M, obtained according to the invention, with reference results AD obtained with an apex-locating device with a commercially available endodontic probe of the prior art. These reference results are indicated in the diagrams showing measurement readings, under the reference AD. In a first aspect of this extensive programme the experimental readings were effected on models of dental root canals, three samples α, β and γ of which are shown in FIGS. 7 to 9.

As shown in FIG. 7 the first dental root canal model (α) has a funnel-shaped orifice extending by a narrow canal with a substantially constant diameter which ends suddenly in an open orifice (shoulder-like recesses).

FIG. 8 shows another dental root canal model (β) having a bifurcation, the root sub-dividing in its terminal part into two root canals β1, β2 and each having an apical orifice, such complex branching existing in the structure of many teeth (molars with multiple roots, premolars with twin roots, etc.).

FIG. 9 shows a final experimental model of a dental root canal (γ) having aberrations and bifurcations with branching into two root canals γ1,γ2 and a lateral excrescence, this type of aberration existing in actual dental roots and being particularly difficult to resolve, i.e. to recognise, single out and distinguish using prior art endodontic probe devices.

Other experimental results plotted in relation to actual teeth will be detailed hereinunder in the following description.

FIGS. 10A to 13'C show a series of measurement results of the apex depth in each of the root canals of the dental models of FIGS. 7, 8 and 9 obtained according to the method of the invention, these results being compared with those obtained with a prior art, commercially available apex-locating device, these comparative results being indicated by a reference mark AD.

For each FIGS. 10, 11, 12-12' and 13-13' the diagrams marked A give the amplitude/depth curves plotted in the presence of an irrigating sodium chloride solution close to 1% (aqueous 0.9% NaCl solution) analogous to "physiological serum" and to the organic fluids such as blood, lymph, saliva or fluids laden with organic debris.

The diagrams marked B and C respectively give curves plotted under the same conditions but in the presence of rinsing solutions based on sodium hypochlorite at a concentration of 2.5% and 5% (10B, 11B, 13B-13'B: 2.5% NaClO) (10C, 12C-12'C, 13C-13'C: 5% NaClO).

The sodium hypochlorite-based ionic alkaline solutions B and C (2.5% and 5% NaClO) are highly conductive. The study relates, in particular, to the influence of these electrolytic solutions on the depth measurement results, their coherence and the choice of the measurement frequencies in order to verify whether the depth measurements correspond to the position of the apex, the existing prior art apex-locating devices (AD) having the great disadvantage of being inoperative under such conditions as the presence of highly conductive solutions, in particular those based on NaClO which is a disinfectant solution (Dakin's liquid, analogous to true Javel water, required during dental procedures).

FIGS. 10A, 11A, 12A, 12A-12'A and 13A-13'A (in the presence of a common saline solution of 0.9% NaCl) show the first results of amplitude curves of the signals as a function of the depth P of the end of the probe or the distance D with respect to the known position of the end of the canal (depth P marked 100, distance D=0) for the three models α, β and γ. As indicated by FIGS. 10, 11, 12 and 13 it appears that the method according to the invention makes it possible to obtain excellent results in determining the depth P of the apex by selecting two amplitude levels If and IF plotted at two particular frequencies, the first at low frequency, i.e. f=100 Hz, and the second at high frequency, i.e. F=0.5 MHz. The two absolute amplitude levels RMS of the intensity I of the frequency signals meet at a point, the position M of which corresponds very precisely to the actual position X of the end of the root canal on the first single-canal dental models (FIG. 10A-11B).

It will be noted in FIGS. 10A to 11B that the precision of the position M of the apex determined according to the invention is measured with a minimum error, below −2% or −3%, which corresponds to a better resolution compared to the margin of error ranging from −8% to +3% given by the commercially available prior art device AD.

Furthermore, and in particular, the plotting of the point of coincidence of the amplitude levels of the alternating signals plotted at the two frequencies f=100 Hz and F=0.5 MHz indicates a measurement M of apex depth which is located very slightly set back (M<100%) before reaching the actual position X of the end of the root canal (negative error of −1% to −3%), while the measurement of position AD indicated by the commercially available prior art device is located sometimes before (AD<<100%) and sometimes beyond (AD>100%) the actual position X of the end of the root canal, which means that the dental procedure can pass the position of the apex, something dentists and patients are absolutely seeking to avoid.

In an advantageous manner in the method of detecting the point of coincidence according to the invention, the choice of a pair of frequencies (f, F) adapted to the presence of physiological liquid, such as a first low frequency f in the no. 2 band around $10^2$ Hz matched with a second high frequency F in the no. 6 band between $0.3 \cdot 10^6$ Hz and $3 \cdot 10^6$ Hz, and more precisely in the octave 0.5 MHz-1 MHz or the higher octave and preferably to a frequency value F of about half to one megahertz makes it possible to obtain excellent apex depth determination results M and especially to obtain a slightly minorated depth which makes it possible to avoid passing the actual position X of the apex.

FIGS. 10B, 10C and 11B relate to amplitude level curves plotted in relation to the tooth model with a single canal α in the presence of an ionic alkaline solution based on 2.5%, 5% and 2.5% NaClO respectively.

The variation in the concentration level of the sodium hypochlorite solution between 2.5% and 5% does not seem to greatly modify the results obtained with the method of detecting the point of coincidence of the levels according to the invention.

It appears that in the presence of sodium hypochlorite, in amplitude diagrams 10B, 10C and 11B, at the start of the introduction of the probe to shallow insertion depths (0<P<<100), the absolute amplitude levels (RMS) of the intensity I of the alternating signals are clearly higher than the levels of the curves in FIGS. 10A and 11A in the presence of 0.9% NaCl saline solution because the NaClO solutions are more highly conductive.

For this reason it appears preferable to select another choice of a pair of low and high frequencies (f, F) to detect the position of the apex with greatest precision in the presence of NaClO.

In the case where sodium hypochlorite solution is present, FIGS. 10B-10C and 11B indicate that it is the intersection of the amplitude levels of the signals determined around the two frequencies, low f=100 Hz and high F=1 MHz or 2 MHz, which gives the best measurement results M for the position of the apex X.

In view of the results of FIGS. 10B, 10C and 11B it appears that the method for measuring the depth position of the apex according to the invention, consisting of detecting the point of coincidence of the two levels determined at low frequency f and high frequency F, in particular at about f=100 Hz and F=1 MH or 2 MHz, indicates a depth position M clearly more precise than the depth measurement results AD determined with the previously available apex-locating device. In particular, the depth position measurements M obtained according to the invention are not augmented with respect to the actual position X of the apex (M<X=100%).

According to the results in FIGS. 10B-10C-11B, in the presence of highly conductive ionic solutions, such as solutions based on 2.5% or 5% NaClO, the choice of a pair of frequencies (f, F) adapted to such solutions, such as a first low frequency f in the no. 2 band around $10^2$ Hz matched to a second high frequency F in the no. 6 band around $10^6$ Hz and more precisely in the octave [1 MHz-2 MHz] or a higher octave and preferably with a frequency value F of about one or two megahertz, makes it possible to obtain excellent results in determining the depth of the apex and especially to obtain a slightly minorated depth M which makes it possible to avoid passing the actual position X of the apex.

FIGS. 12C-12'C and 13B-13'B, 13C-13'C give amplitude level curves and the depth position measurements M plotted in the presence of sodium hypochlorite (marks B: 2.5% NaClO and C: 5% NaClO) for such a choice of defined frequencies on the tooth models β and γ having complex root canals, more specifically forked root canals or branched root canals with aberrations.

Diagrams 12A and 12C correspond to the apex depth measurements on the first canal β1 of the dental model β of FIG. 8.

Diagrams 12'A and 12'C correspond to the depth measurements of the other apex in the second canal 132 of the model β in FIG. 8.

Diagrams 13A, 13B and 13C correspond to the depth measurements of the apex in the first root canal γ1 of the last dental canal model γ shown in FIG. 9.

Diagrams 13'A, 13'B and 13'C correspond to the depth measurements of the other apex in the other root canal γ2 of the model γ of FIG. 9.

It appears that the prior art apex-locating device AD gives no measurement result (AD=0 or an "error of −100%") on these complex root canal models having root bifurcations or aberrations. The prior art device AD gives no indication of the depth of the ends of the root canals on either of the branched root canals. The device does not provide a usable result either in the presence of NaCl saline solution (FIG. 12A: β1, 0.9% NaCl, no indication of measurement; FIG. 12'A: β2, 0.9% NaCl: overestimated depth indication to be avoided; FIG. 13A: γ1, 0.9% NaCl: excessive depth indication; FIG. 13'A: γ2, 0.9% NaCl: no result).

On these same complex models β and γ of branched root canals β1-β2 and γ1-γ2 the depth position measuring method according to the invention gives precise, coherent measurements M of the depth position of the end of each of the two root canals β1-β2 or γ1-γ2 with a low relative error and does not indicate any excessive measurement of augmented or overestimated depth which would be beyond the actual position X of the end of the corresponding root canal.

In a particularly advantageous manner according to the invention, the method for measuring the depth position of the apex, i.e. of the end of the root canal of a tooth, makes it possible to resolve the root canals of complex teeth having bifurcations and/or aberrations. The method according to the invention makes it possible to measure the depth M of each of the root canals with a good level of precision and avoiding augmented measurement indications which would be beyond the apex X in the ligament below the root of the tooth, which achieves the object desired by dentists for their patients.

The final aspect of the measurement programme consists of verifying the application of the method for measuring the depth of the apex on actual teeth.

FIGS. 14A, 14B and 14C show a series of measurement curves and results obtained on an actual tooth Δ with the choices of the pairs of defined frequencies as indicated above and in the presence respectively of irrigating solutions of 0.9% NaCl and 2.5 and 5% NaClO.

As shown in FIG. 14A, the apex depth measuring method according to the invention gives equally good measurements M of the depth of the apical constriction of the tooth Δ in the presence of a sodium chloride solution (0.9% NaCl) with excellent precision of within one percent.

And above all, in a particularly advantageous manner, in the presence of a sodium hypochlorite-based conductive disinfectant solution (FIG. 14B: 2.5% NaClO and FIG. 14C: 5% NaClO), while the prior art apex-locating device AD gives no measurement indication (AD=0 "error −100%"), the method according to the invention makes it possible to obtain excellent depth position measurements of the apex of the actual tooth Δ with a precision of within one percent (error less than 1% and estimated at less than 0.1% or 0.6%).

In a more general way it appears that the choice of frequency values (f, F) is crucial in ensuring that the point of coincidence M of the two absolute amplitude levels of the alternating signals measured at the two lower and higher frequencies f and F corresponds exactly to the actual position X of the apex and in obtaining precise measurements M of the depth position of the apex at the end of the root canal of a tooth.

FIGS. 15 to 18 show diagrams synthetically grouping the error $\epsilon_{err}$ of the apex depth measurements M as a function of the higher frequency F used when applying the apex-locating method of the invention.

Each of the diagrams 15 to 18 shows the rate of error $\epsilon_{err}$ of each apex depth measurement M according to the invention depending on the selected higher frequency value F produced by the frequency generator GF, the lower frequency value f being fixed in this case at a low frequency value f=100 Hz.

The measurement error $\epsilon_{err}$ is the deviation between the measurement M of the position of the coincidence point obtained in accordance with the invention and the actual depth X of the end of the root canal measured metrically on dental models α, β, γ or on tooth specimens A.

The rate of error $\epsilon_{err}$ is expressed as a percentage with respect to the exact length of each root canal of a dental model α, β, γ or of an actual tooth Δ, i.e. as a percentage of the actual depth of the apex.

FIG. 15 brings together the depth error values plotted in relation to the depth measurements effected on the dental root canal model α of FIG. 7, several measurement results of which have been shown in FIGS. 10A to 11B.

FIG. 16 shows the error values of the depth measurements obtained on the dental canal model β of FIG. 8 (measurement results illustrated in FIGS. 12A-12'A and 12C-12'C).

FIG. 17 shows the error values $\epsilon_{err}$ of the depth measurements M effected on the dental canal model γ of FIG. 9 (cf. measurement results shown in FIGS. 13A to 13'C).

FIG. 18 indicates the error values $\epsilon_{err}$ plotted in relation to a series of depth measurements M effected on six actual teeth (not shown) and the measurement results of which are shown in FIGS. 14A to 14C.

These depth measurements were carried out according to the invention with a lower frequency of value f=100 Hz and higher frequency values F assuming selected defined values between 200 kHz and 5 MHz, in particular at frequency values of 500 kHz, 1 MHz, 2 MHz etc, thus including the whole of conventional frequency band no. six which covers the frequencies ranging from 300 kHz to 3 megahertz, extending if appropriate into the two adjacent bands number five (30 kHz to 300 kHz, around $10^5$ Hz) and number seven (3 MHz to 30 MHz, around $10^7$ Hz), conventionally.

It appears that in such frequency bands it is possible to achieve low measurement errors $\epsilon_{err}$ clearly lower than ten percent and even less than or of the order of one or a few percent. More precisely, the measurement error $\epsilon_{err}$ decreases regularly as the higher frequency value F increases, and passes from positive error values $\epsilon_{err}>0$ for frequencies F between 200 kHz and 500 kHz to negative error values $\epsilon_{err}<0$ for frequencies F of the order of 1 or 2 MHz to 5 MHz and more.

Of course, an effort is made to minimise the measurement error $\epsilon_{err}$ and also, as stated previously, it is preferable for practitioners to have a negative error measurement $\epsilon_{err}<0$, i.e. to obtain slightly minorated apex depth measurements M (i.e. P underestimated: M<X=100%) rather than risk having a positive error $\epsilon_{err}>0$ and running the risk of passing the actual position of the apical terminus.

According to the diagrams in FIGS. 15 to 18 it appears that according to the experimental embodiments of the invention as set out herein:

In the presence of a common aqueous saline solution: (0.9% NaCl) the apex position X corresponds to the point M of coincidence or intersection C of the first amplitude level of the alternating signal determined at the lower frequency f (f=100 Hz) with the second amplitude level of the signal measured at a higher frequency F within the band of from 200 kHz to 2 megahertz or in the conventional number six band (i.e. between 300 kHz and 3 MHz) and more particularly close to frequencies F of from 500 kHz to 1 MHz or in the adjacent frequency octaves (i.e. from 250 to 500 kHz, from 500 kHz to 1 MHz and/or from 1 MHz to 2 MHz).

In the presence of a sodium hypochlorite-based aqueous disinfectant solution (Dakin's solute; 2.5% or 5% NaClO) the position X of the apex corresponds to the point M of intersection or coincidence C of the first signal amplitude level determined at the lower frequency f (f ~100 Hz) with a second signal amplitude level obtained at a higher frequency F in the conventional band number six or higher (from 300 kHz to 3 MHz and more), in particular in a frequency band F ranging from 500 kHz to 5 MHz and more precisely in the octave of the frequencies between 1 megahertz and 2 megahertz or possibly in one and/or the other of the adjacent frequency octaves (i.e. from 0.5 MHz to 1 MHz and/or from 2 MHz to 4 MHz).

FIG. 18 shows that these results and the refinement of the range of selected frequencies for the measurements are coherent and in concert with a whole series of results of measurements carried out on actual teeth. It appears that the choice of the pair of frequencies (f, F) permitting detection of the point of coincidence C of the two amplitude levels If and IF and measurement of the depth of the apex is effected according to the nature of the irrigating solution:

in the presence of 0.9% NaCl, the higher frequency F is preferably selected within the frequency range of 200 kHz to 5 MHz, in particular in the conventional number six band (frequency from 300 kHz to 3 MHz) and more precisely in the octave of frequencies around 0.5 MHz to 1 MHz or in one and/or the other of the adjacent frequency octaves (from 0.25 MHz to 0.5 MHz and/or from 1 MHz to 2 MHz).

In the presence of sodium hypochlorite-based antiseptic solution the depth of the apex corresponds to the point of coincidence or intersection between the first level determined at the lower frequency f around 100 Hz and a second level measured at a higher frequency F chosen in a frequency band between 500 kHz and 5 megahertz or in the conventional number six band and more precisely around a frequency octave between 1 MHz and 2 MHz and/or in one and/or the other of the adjacent frequency octaves (from 0.5 MHz to 1 MHz and/or from 2 MHz to 4 MHz).

According to the invention it is thus possible to produce an apex-locating system having a frequency calibre control making it possible to adjust the higher frequency value F to a calibrated value among a set of preselected frequency values, for example to a value selected from a set of frequency values such as {0.5 MHz; 1 MHz; 2 MHz; 5 MHz} or other sets of similar frequencies selected in the adjacent frequency bands or octaves. A frequency calibre control such as this may alternatively relate to the choice of the lower frequency value f. It is also possible to provide two frequency calibre controls, one relating to the choice of the lower frequency f, the other to the choice of the higher frequency F. Such provisions make it possible to facilitate the procedures of the practitioner who can actuate the calibrated control with reference only to the nature of the irrigating solution he/she is injecting into the root canal.

The frequency selection commands to excite the circuit at the first lower frequency and at the second higher frequency, the measurements of the absolute amplitude levels of the intensity of the electrical frequency signals in the said circuit, and the detection of the point of coincidence are preferably effected automatically within the device by a microprocessor or a microcontroller or more generally by a computing unit, programmed to this effect, so as to emit a signal (sound or light) in order to warn the practitioner when the first level measured at the first lower frequency is no longer higher than the second electrical magnitude level of the alternating signal measured at the second higher frequency.

Figure 1:
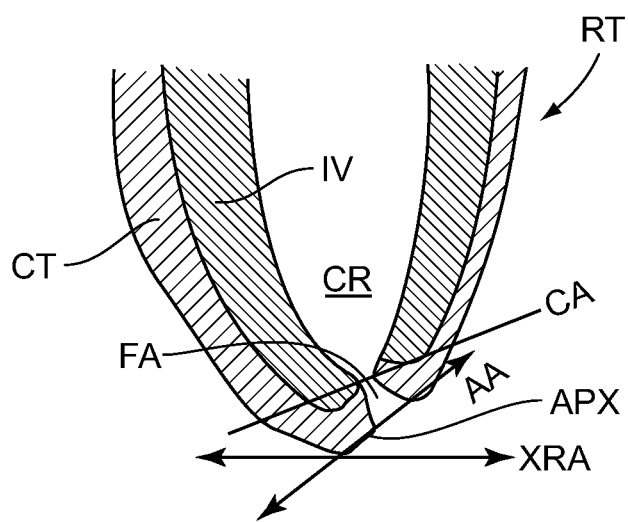
Figure 2:
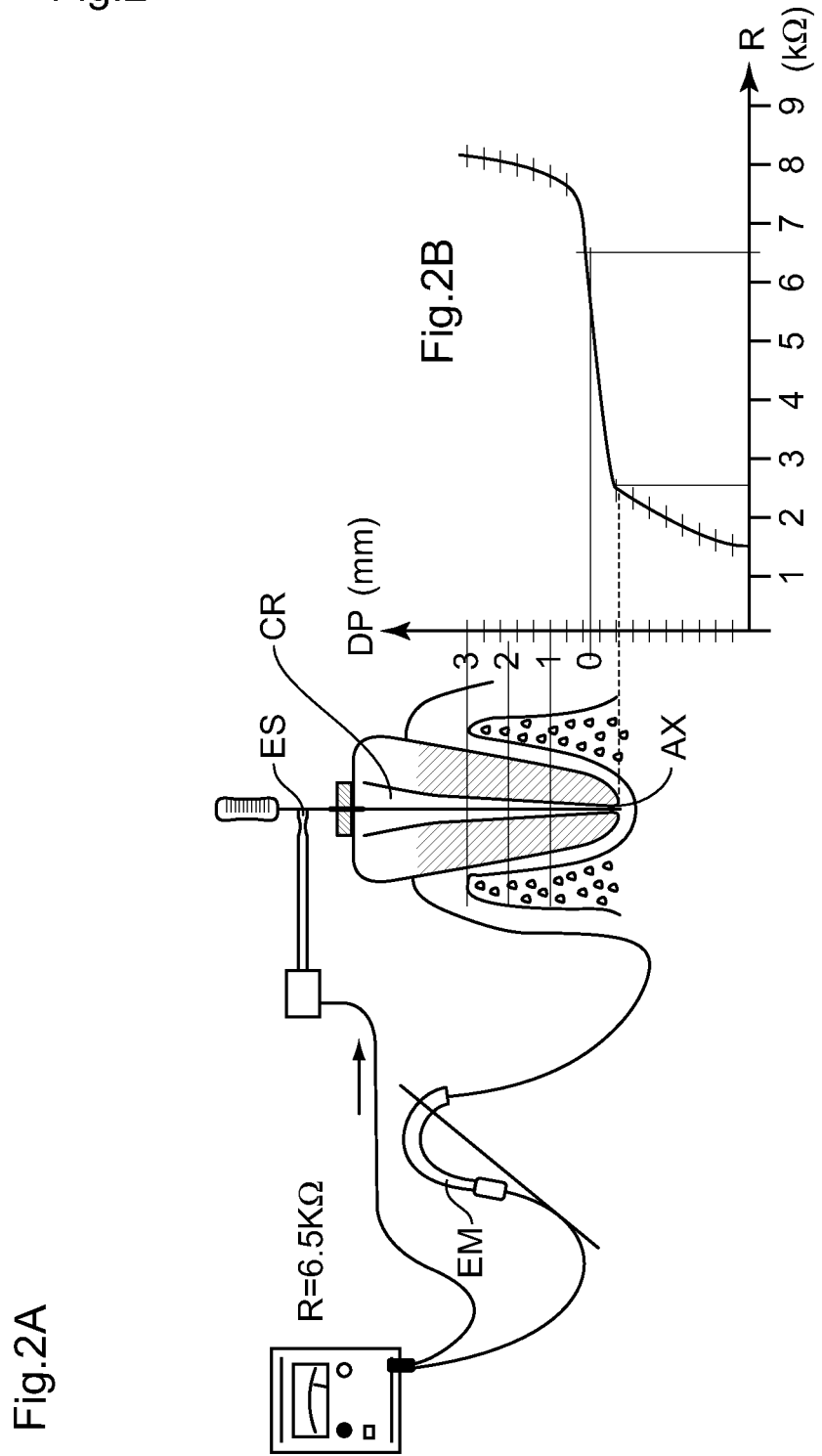
Figure 3:
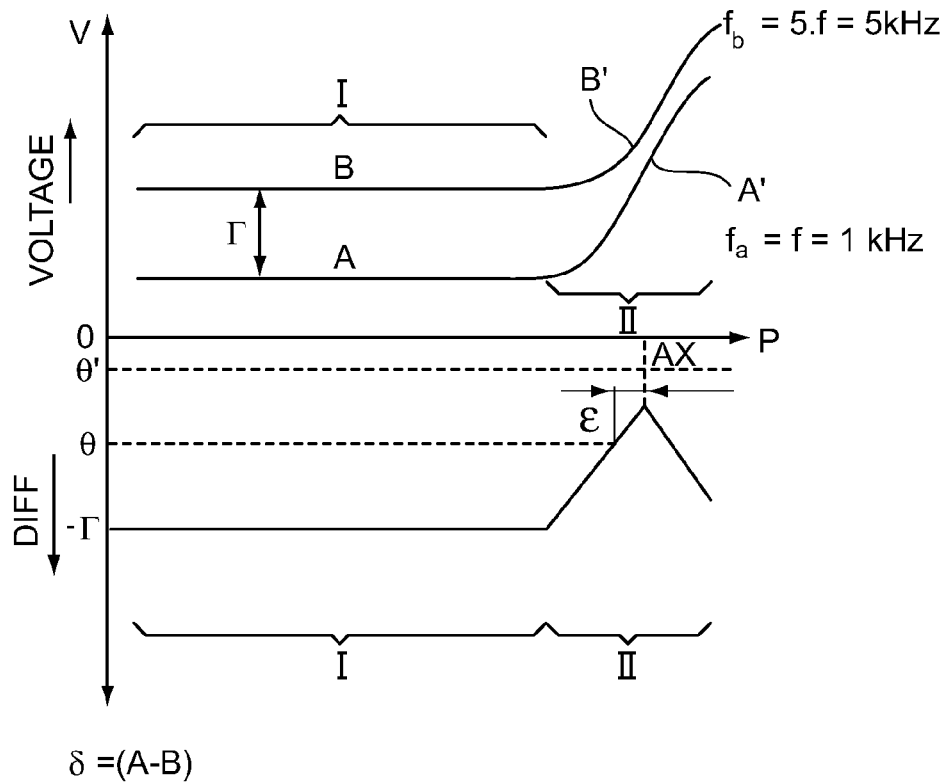
Figure 4:
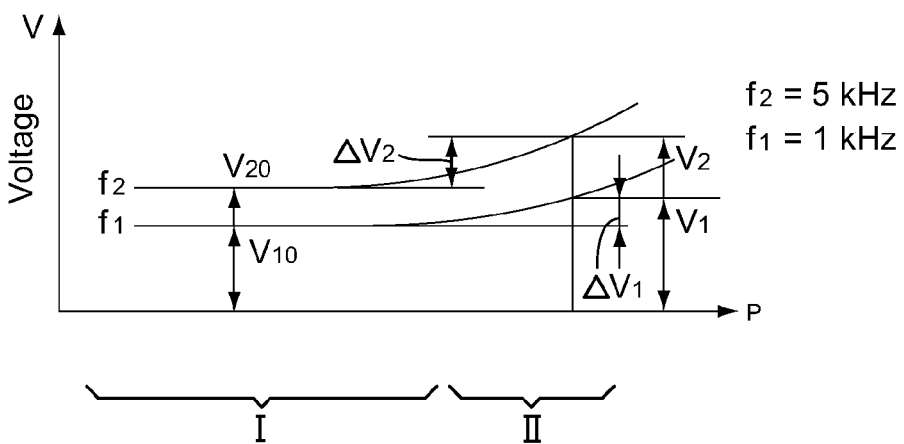

In fact it appears, contrary to the teaching of the documents U.S. Pat. No. 5,080,586 and U.S. Pat. No. 5,096,419 (cf. FIGS. 3 and 4), that in the pair of opposing frequencies (f, F) used according to the invention, the lower frequency f and the higher frequency F are selected so that in the initial phase I at the start of insertion of the point of the probe at the start of the root canal CR or of the crown-like part of the tooth, the first amplitude level If=I1 determined at the lower frequency f is higher, clearly higher, than the second amplitude level IF=I2 determined at the second higher frequency F.

According to an alternative embodiment of the invention it is possible to locate the apex by proceeding as follows:

while the first absolute amplitude level If of the intensity of the alternating signal determined at the lower frequency f is higher than the second level IF determined at the higher frequency F, the end of the probe has not reached, nor passed, the position of the apex X and the result of the detection test is negative (no apex detection signal)

as soon as the first absolute amplitude level If, determined at the lower frequency f, is not, or is no longer, higher than the second level IF determined at the higher frequency F (i.e. the second level IF→I4 is higher or substantially equal to the first level If→I3), the detection test is positive and the detection means of the device can trigger the emission of a signal to warn the practitioner.

The lower and higher frequency values (f, F) indicated herein are data given solely by way of non-limiting embodiments, other frequency pairs being definable by experimentation, for example, by modifying the value of the first lower frequency f, in particular in order to select other lower frequency values in radio band no. 2 or 3 or in frequency bands lower than 100 Hz or band no. 2 and/or by selecting other higher frequency values F, in particular, other higher frequencies F matched with such lower frequency values f.

The invention claimed is:

1. Apex-locating method for determining a measurement (M) of the depth position of the apex in a root canal of a tooth (α, β, γ, Δ), using a device comprising a first conductive electrode (E1) forming an endodontic probe (S) able to be inserted into the root canal (CR) of a tooth, a second electrode (E0) shaped to be brought into electrically conductive contact with an oral mucous membrane, frequency-generating means (GF) able to produce alternating electrical signals at a number of frequencies, and means (AM) for measuring the magnitude of alternating electrical signals in a circuit comprising said frequency generator, the first probe electrode inserted into the root canal and the second electrode in contact with the oral mucous membrane, said method comprising the steps of:

exciting the circuit and measuring the levels of magnitude (I) of the alternating electrical signals in the circuit, respectively at a lower frequency (f) and at a higher frequency (F); and detecting a point of coincidence (C) where two respective levels (If, IF) of the electrical magnitude (I) measured at said lower and higher frequencies (f, F) meet and are substantially equal, said lower and higher frequencies (f, F) being sufficiently far apart for such a point of coincidence (C) to exist, said point of coincidence (C, M) corresponding to the position (X) of the apex.

2. Apex-locating method as claimed in claim 1, characterised by measuring amplitude levels of the electrical signals applied to the circuit and/or the intensity (I) of the current passing through the electrodes (E0-E1).

3. Apex-locating method as claimed in claim 2, characterised by measuring absolute voltage amplitude values (U=Rm.I) of the electrical signals at the terminals of a resistor (Rm) in series with the electrodes (E0-E1-S).

4. Apex-locating method as claimed in claim 1, characterised in that the lower frequency (f) and the higher frequency (F) are selected so that in an initial phase (I), corresponding to the commencement of the insertion of the end of the endodontic probe electrode (E1-S) at the beginning of the root canal (CR), the first level (If=I1) measured at the lower frequency (f) is higher than the second level (IF=I2) measured at the higher frequency (F).

5. Apex-locating method as claimed in claim 1, characterised in that the lower and higher frequencies (f, F) are selected in opposing frequency bands (BF, HF) which are non-adjacent.

6. Apex-locating method as claimed in claim 1, characterised in that said lower and higher frequencies (f, F) are separated by one or more orders of magnitude.

7. Apex-locating method as claimed in claim 1, characterised in that said lower frequency (f) is selected in a low frequency band (BF) while said higher frequency (F) is selected in a high frequency band (HF).

8. Apex-locating method as claimed in claim 1, characterised in that said lower frequency (f) and said higher frequency (F) are located respectively in two opposing frequency ranges (BF, HF) on either side of a frequency range including at least the conventional number four band (VLF or hm.W.B. or no. 4) which covers the frequencies of three kilohertz to thirty kilohertz (3-30 kHz).

9. Apex-locating method as claimed in claim 1, characterised in that the lower frequency (f) is lower than 950 hertz.

10. Apex-locating method as claimed in claim 1, characterised in that the higher frequency (F) is higher than 9500 hertz.

11. Apex-locating method as claimed in claim 1, characterised in that the lower frequency (f) is located between 300 hertz and 30 hertz.

12. Apex-locating method as claimed in claim 1, characterised in that the higher frequency (F) is located between 300 kHz and 3 MHz.

13. Apex-locating method as claimed in claim 1, characterised in that the lower frequency (f) is in a frequency band of ten hertz to 100 hertz, while the higher frequency (F) is selected in a frequency band of the order of one half megahertz to ten megahertz, adjusting the choice of the higher frequency (F) to a value selected among a group of plural calibrated values depending on the electrolytic conditions prevailing in the root canal (CR).

14. Apex-locating method as claimed in claim 1, characterised in that the lower frequency (f) is lower than 500 hertz.

15. Apex-locating method as claimed in claim 1, characterised in that the higher frequency (F) is higher 95 kHz.

16. Apex-locating method as claimed in claim 1, characterised in that,
the lower frequency (f) is in a frequency band of ten hertz to 100 hertz,
the higher frequency (F) is selected in a frequency band of the order of one half megahertz to ten megahertz, and
the higher frequency (F) is adjusted to a value selected among a group of plural calibrated values around 0.5 MHz, 1 MHz, 2 MHz, and 5 MHz, depending on the electrolytic conditions prevailing in the root canal (CR), including the presence of a conductive aqueous ionic solution.

17. Apex-locating method as claimed in claim 16, characterised in that the conductive aqueous ionic solution includes one of a physiological liquid based on a saline solution of sodium chloride (NaCl) or a Dakin's liquid based on a disinfectant solution by sodium hypochlorite (NaClO).

18. Apex-locating method as claimed in claim 1, characterised in that the lower and higher frequencies (f, F) are selected in opposing frequency bands (BF, HF) which are distinct.

19. Apex-locating method as claimed in claim 1, characterised in that said lower and higher frequencies (f, F) are separated by four orders of magnitude.

* * * * *